United States Patent
Reel et al.

(10) Patent No.: US 7,709,808 B2
(45) Date of Patent: May 4, 2010

(54) SYSTEMS, METHODS AND APPARATUS FOR SINGLE MOLECULE SEQUENCING

(75) Inventors: Richard T. Reel, Hayward, CA (US);
Mark F. Oldham, Los Gatos, CA (US);
Eric S. Nordman, Palo Alto, CA (US);
Steven J. Boege, San Mateo, CA (US);
Steven M. Menchen, Fremont, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 11/749,411

(22) Filed: May 16, 2007

(65) Prior Publication Data
US 2008/0105831 A1 May 8, 2008

Related U.S. Application Data

(60) Provisional application No. 60/800,440, filed on May 16, 2006.

(51) Int. Cl.
*G01N 21/64* (2006.01)
(52) U.S. Cl. .................................. 250/458.1
(58) Field of Classification Search ............. 250/458.1, 250/483.1, 368, 487.1, 459.1; 359/569; 422/82.08, 422/82.11
See application file for complete search history.

(56) References Cited

U.S. PATENT DOCUMENTS

| | | | |
|---|---|---|---|
| 5,776,785 A * | 7/1998 | Lin et al. | 436/527 |
| 5,882,472 A | 3/1999 | Vernon et al. | |
| 2003/0044781 A1* | 3/2003 | Korlach et al. | 435/6 |
| 2004/0041082 A1* | 3/2004 | Harmon | 250/214 R |
| 2004/0046128 A1* | 3/2004 | Abel et al. | 250/458.1 |
| 2005/0221279 A1* | 10/2005 | Carter et al. | 435/4 |

FOREIGN PATENT DOCUMENTS

WO  WO 2005/003743   1/2005

OTHER PUBLICATIONS

Axelrod, "Total Internal Reflection Fluorescence Microscopy in Cell Biology", Traffic, 2001, vol. 2, pp. 764, Aug. 20, 2001.
PCT International Preliminary Report on Patentability for Application No. PCT/US07/069026, dated Nov. 17, 2008, 5 pages.

* cited by examiner

*Primary Examiner*—David P Porta
*Assistant Examiner*—Faye Boosalis
(74) *Attorney, Agent, or Firm*—Life Technologies Corporation

(57) ABSTRACT

An embodiment generally relates to a system for analysis of an analyte. The system can include a transparent substrate. The system also includes an excitation light source configured to induce an evanescent wave excitation of a fluorescently labeled molecule near the access to the transparent substrate and a detector for detecting the fluorescently labeled molecule.

20 Claims, 20 Drawing Sheets

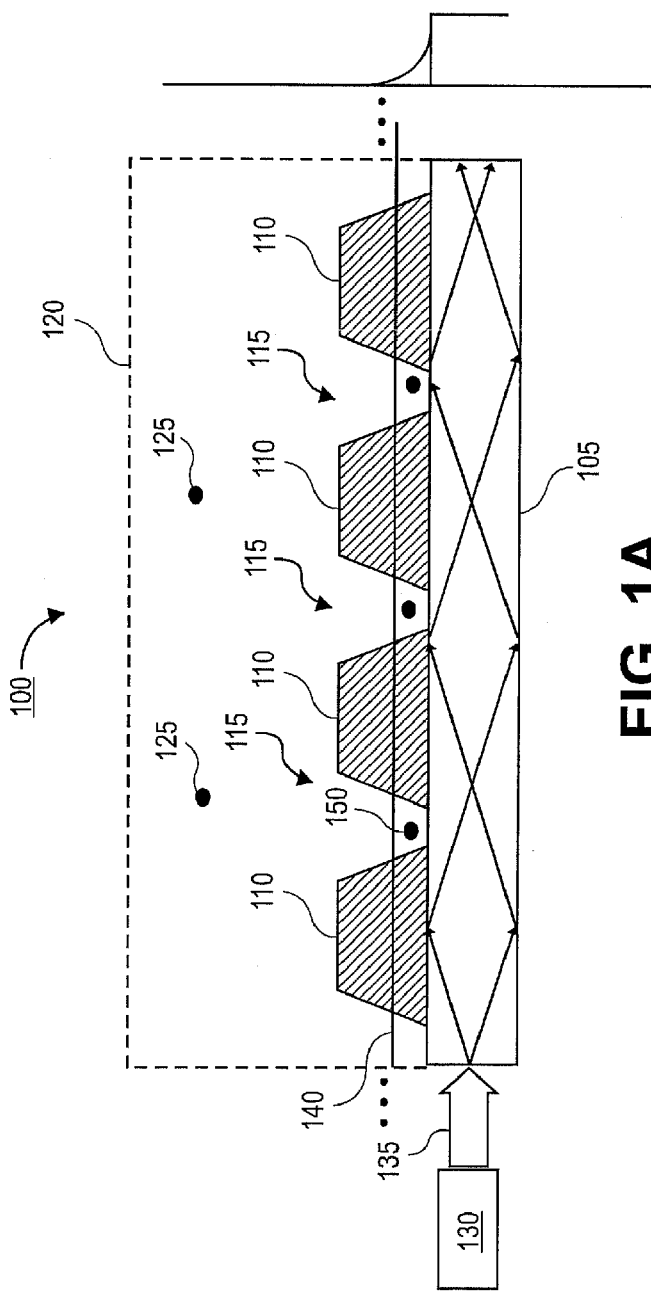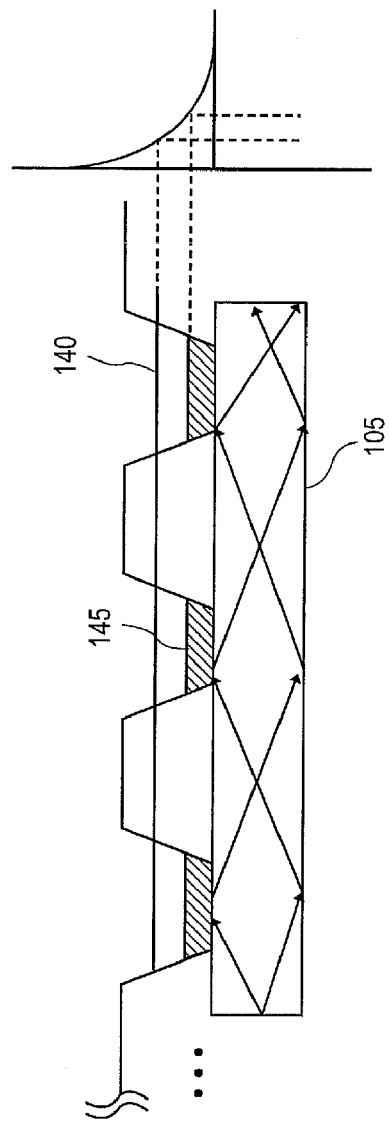

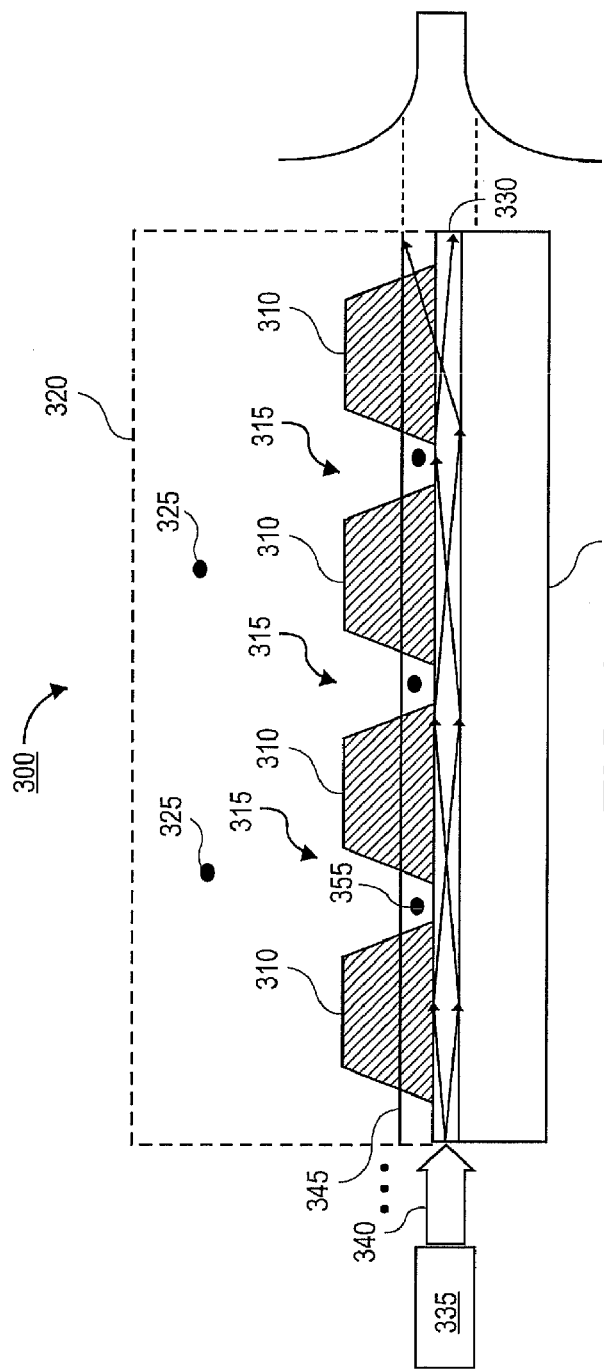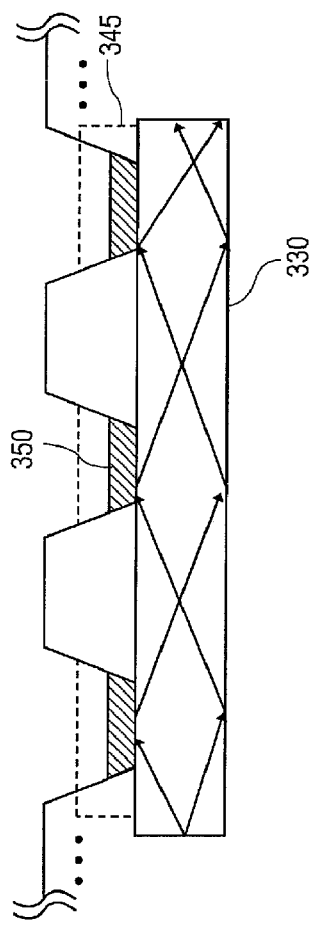
FIG. 3A
FIG. 3B

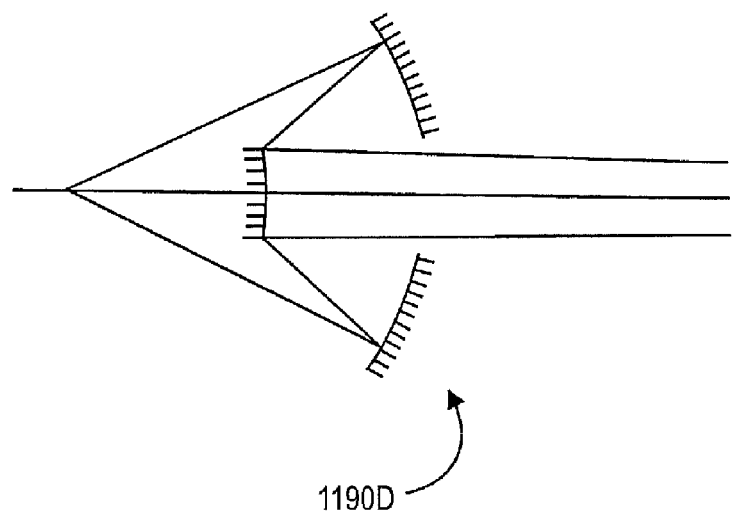
1190D
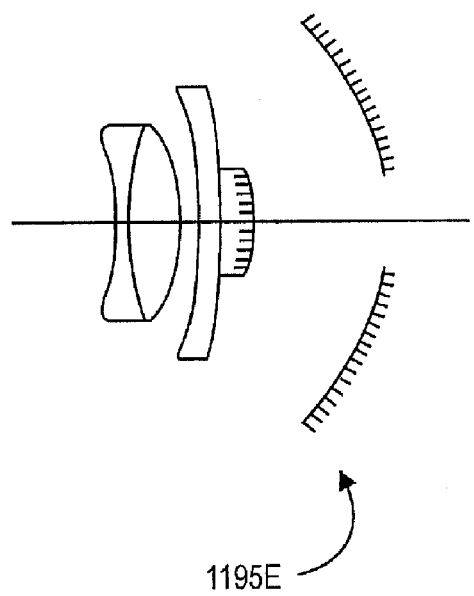
1195E
FIG. 11E

SYSTEMS, METHODS AND APPARATUS FOR SINGLE MOLECULE SEQUENCING

RELATED APPLICATIONS

The present application claims priority to U.S. Provisional Application No. 60/800,440 entitled "Systems, Methods, And Apparatus For Single Molecule Sequencing" filed on May 16, 2006 and is hereby incorporated by reference for all purposes.

FIELD

This invention relates generally to single molecule sequencing, more particularly, to detecting single molecules without the use of zero-mode waveguides.

DESCRIPTION OF THE RELATED ART

It is generally significant to reduce the background in assay systems for the detection of single molecule events. The background can come from the high concentration of labeled nucleotides in the detection volume. U.S. Patent Application 20030044781 ('781 Application), which is hereby incorporated by reference in its entirety, describes a method of sequencing target nucleic acids having a plurality of bases. The '781 application describes the use of a zero-mode waveguide, a waveguide that is approximately ten times smaller than the selected wavelength, to preclude propagation of light into a fluid, and consequently limit the excited volume.

SUMMARY

An embodiment generally pertains to a system for analysis of an analyte. The system can include a transparent substrate. The system can also include an excitation light source configured to energize a fluorescently labeled molecule by an inorganic absorber and a detector configured to detect the fluorescently labeled molecule.

Another embodiment relates generally to a system for analysis of analyte. The system can include a transparent substrate coated with a metal layer and an exclusion coating deposited on the metal layer. The system can further include a fluorescent labeled molecule configured to diffuse into holes of the exclusion coating and an excitation light source configured to produce plasmon-coupled emission excitation at a substrate side of the exclusion coating.

Yet another embodiment pertains generally to a luminescence detection system. The system includes a resonant optical cavity where luminophore emission is elicited by evanescent excitation established at the boundary of a resonant optical cavity.

BRIEF DESCRIPTION OF THE DRAWINGS

Various features of the embodiments can be more fully appreciated, as the same become better understood with reference to the following detailed description of the embodiments when considered in connection with the accompanying figures, in which:

FIG. 1A illustrates a side view of an excitation device in accordance with an embodiment;

FIG. 1B illustrates a more detailed view of an excitation zone;

FIG. 3A illustrates a side view of another excitation device in accordance with an embodiment;

FIG. 3B illustrates a more detailed view of an excitation zone in the excitation device shown in FIG. 3A;

FIG. 11E illustrates exemplary reflective and catadroptric lenses;

Figure 2:
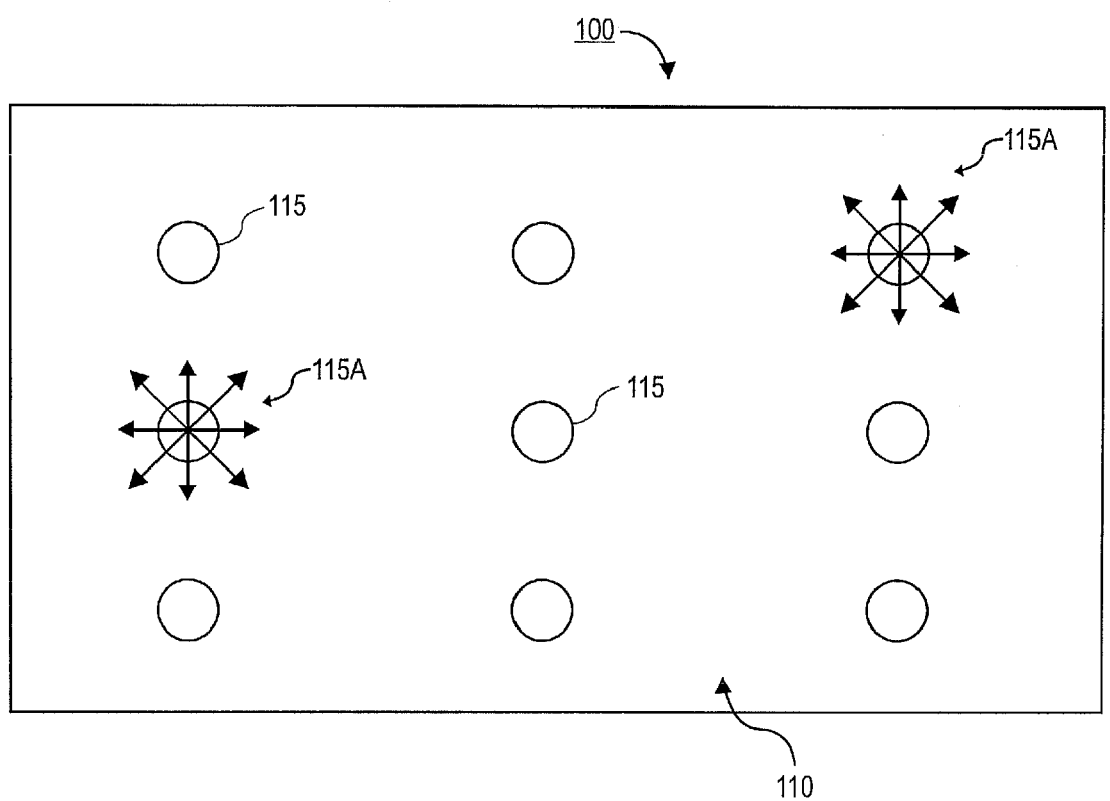
FIG. 2 illustrates a top view of a section of the excitation device shown in FIG. 1.

It should be readily apparent to those of ordinary skill in the art that the figures depicted herein represent a generalized schematic illustration and that other components may be added or existing components may be removed or modified.

DETAILED DESCRIPTION OF EMBODIMENTS

For simplicity and illustrative purposes, the principles of the present invention are described by referring mainly to exemplary embodiments thereof. However, one of ordinary skill in the art would readily recognize that the same principles are equally applicable to, and can be implemented in, all types of assay systems, and that any such variations do not depart from the true spirit and scope of the present invention. Moreover, in the following detailed description, references are made to the accompanying figures, which illustrate specific embodiments. Electrical, mechanical, logical and structural changes may be made to the embodiments without departing from the spirit and scope of the present invention. The following detailed description is, therefore, not to be taken in a limiting sense and the scope of the present invention is defined by the appended claims and their equivalents.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

One embodiment generally relates to systems and methods for detecting single molecule events. More specifically, an excitation device using internal reflection to prevent light from entering a fluid. The excitation device can include a substrate and a coating. The substrate can be a transparent material such as fused silica, glass, and or crystalline materials. A coating can be applied to the substrate. The coating can be transparent, semi-opaque or opaque and should have a lower index of refraction than the substrate. Microscopic holes can be implemented within the coating. An analyte fluid can be placed on the excitation device. An excitation light source, e.g., a laser at a selected frequency, is directed into the substrate and reflects off the coating and fluid in the microscopic holes by total internal reflection (TIR). This reflection creates an evanescent wave extending into the coating and its respective holes. The intensity of this evanescent wave quickly decays from the substrate surface. In some instances, the coating can be referred to as an exclusion coating since molecules are excluded from the excitation light except in the desired locations, typically, the microscopic holes.

Accordingly, this evanescent wave excitation can only illuminate the analyte fluid that is close to the substrate of the excitation device. Because the evanescent wave intensity quickly decays from the substrate surface the coating can form a barrier that impedes the analyte fluid, i.e. dye molecules, from reaching the excitation except at the bottom of the holes where the analyte fluid is close to the substrate. Moreover, if the coating is transparent, light may be collected from above, below or both sides of the substrate surface. The substrate surface in the detection area is preferentially a plane but could be non-planar if advantageous for imaging. An example of a non-planar substrate surface can be a substrate implemented with multiple layers, where the layers can be different materials with respective and appropriate indices of refraction.

Other embodiments pertain generally to a method of creating an energy transfer zone to locate the "useful" excitation zone to a smaller zone in proximity to an excitation light converter, where the excitation light converter is chemically attached to the substrate. More specifically, embodiments may include at least one quantum dot as an excitation light converter that absorbs light and transfers it to the labeled moiety of interest. The transfer of energy can involve a wavelength shift. The labeled moiety would then typically emit at a longer wavelength. In other embodiments, quantum dots of differing size can be used for different wavelengths.

In other embodiments involving two-photon excitation, the light can emit at a shorter wavelength than the excitation wavelength. This is typically done by using pulsed laser excitation to assure that two photons can excite the fluorescent label in short time. Since the emission light is at a shorter wavelength than the excitation, it is easier to reject the background by filtering, as the background is typically at a longer wavelength than the excitation. The wavelength of fluorescence of photons emitted by dye molecules is typically a longer wavelength than the wavelength of the excitation photons that elicited the fluorescent emission.

Two-photon excitation may utilize either standard fluorophores, or may utilize up-converting phosphors. An up-converting phosphor is made of mixed-metal oxide nano-powders, including rare earth oxides. $Y_2O_3$:Yb, Er, $Y_2O_2$S:Yb, Er, $Y_2O_2$S:Yb, Ho, and $Y_2O_2$S:Yb, Tm, lanthanide compounds, are examples from the literature. Unlike quantum dots or standard fluorophores, the emission light is a shorter wavelength than that of the excitation light, and thus has the advantages previously described for two-photon fluorophore excitation, while retaining the narrow emission bands and photo stability of quantum dots. Up-converting phosphors can be made in various sizes, including powders as small as 20 nm. As such, they can be used in manner similar to that of quantum dots, and thus any place where the term quantum dot is used hereafter, it may also refer to an up-converting phosphor, except where a quantum dot is described.

The energy transfer for two-photon excitation can occur non-radiatively via an induced dipole-dipole interaction. Alternatively, the energy transfer can occur by radiative coupling. However, radiative coupling can result in a larger excitation zone since radiative coupling drops by $1/R^2$ vs. $1/R^6$ for dipole-dipole interaction. Moreover, radiative coupling can emit light that needs to be rejected or screened. This shift in the emission wavelength allows filters to block both excitation sources during detection. The blocking of the filters can be removed during part of the process to allow target position determination.

Quantum dots can be made to provide a desired second excitation since quantum dots produce a wavelength dependent on the size of the dot. Moreover, quantum dots can have a narrower spectral emission, shorter spectral tails and a wider absorption band than FRET dyes.

FIG. 1A illustrates a side view of an excitation device 100 in accordance with an embodiment. As shown in FIG. 1, the excitation device 100 can include a substrate 105 and an exclusion coating 110. In some embodiments, the substrate 105 and the exclusion coating 110 can be implemented with material having low fluorescence characteristics to minimize background noise. In other embodiments, the substrate 105 can be further specified to be fused silica (n=1.47), crystal quartz (n=1.543) or other type of low fluorescent glass, plastic or combinations thereof.

In yet other embodiments, the substrate 105 can be implemented with high index of refraction materials such as $Ta_2O_5$ (n=2.1) or $TiO_2$ (n=2.5-2.9). The use of high index materials in the substrate 105 can facilitate a light guiding layer for excitation light propagation. The light can be coupled into the light guiding layer using a prism or grating, as described later with respect to FIG. 3AB. The exclusion coating 105 can be deposited on this light guiding layer. Moreover, high-index of refraction substrates can allow more exclusion coating 110 options as the coating and fluid index must be less than the substrate. In various other embodiments, the evanescent wave can drop faster to reduce the required exclusion coating thickness because a rapid change in the index of refraction for material reduces the evanescent wave penetration depth 140.

The implementation of the exclusion coating 110 can be dependent on the index of the substrate 105 or light guiding layer 330. More particularly, for high index substrates, many lower index materials may be selected. For example, PMMA (n=1.491), polycarbonate (n=1.586), cyclic polyolefin (n=1.525) and other similar materials can be selected for the exclusion coating. In some embodiments, optical exclusion coatings such as $MgF_2$ or glasses such as $SiO_2$ having an index less than the substrate 105 can also be used. In yet other embodiments, the exclusion coating 110 can be implemented using fused silica (n=1.47), Teflon FEP (n=1.341-1.347), Teflon AF (n=1.32), $MgF_2$ (n=1.38) may be used.

The exclusion coating 110 can be transparent or opaque. The exclusion coating 110 can also be partially absorbing, reflective, or selectively reflective. For embodiments with opaque exclusion coatings and other types of exclusion coatings, unwanted light from the sample outside a hole is attenuated. Unwanted light can occur if the exclusion coating 110 or substrate 105 is not properly formed resulting in leakage of excitation light 135 too far into the analyte fluid and reaching sample 120. For embodiments with transparent exclusion coatings, emissions can be collected from the side that interfaces with the analyte fluid sample 120, the substrate side or both sides simultaneously. This is also possible with multi-layer structures.

Holes (or slots, channels, wells, etc.) 115 can be formed within the exclusion coating 110 to allow the analyte fluid sample 120 to interface with the substrate 105. In some embodiments, the analyte fluid sample 120 can contain a dye labeled nucleotide with a non-fluorescent quencher 125 on the triphosphate, i.e., dNTP. Placing a non-fluorescent quencher 125 on the triphosphate quenches the dye label. When incorporated into the DNA strand, the quencher is cleaved and the fluorescent dye lights up where all other free nucleotides are dim. Exclusion coating 110 can be configured to exclude molecules from the excitation light except in desired locations defined by the hole 115 or the pattern of holes 115. Thus, the excitation light can only efficiently excite fluorescent molecules at the bottom of a hole 115.

For certain embodiments, the volume of the hole 115 can be small enough to control background noise from diffusion events. For example, fluorescently labeled nucleotides at standard concentrations can be accomplished with holes 115 sized between 30-150 nm or larger in diameter. Lower concentrations of labeled dNTPs can enable the user of larger holes.

Although the holes 115 are depicted in side view in FIG. 1A, it should be readily obvious to those skilled in the art that the shape of the holes 115 may be circular, rectangular, elliptical, or any other three dimensional shape. In some other embodiments, the holes 115 may have non-vertical sides such as tapered or curved sides. For exclusion layer implementations using multi-layer structures, the holes 115 can be configured by creating a larger hole, reapplying another exclusion layer and thus creating small holes. Other methods of creating holes 115 are known to those skilled in the art.

The excitation device 100 can be in contact with the analyte fluid sample 120. The analyte fluid sample 120 can contain dyes, nucleotides, and other materials (e.g., dye labeled nucleotide non-fluorescent quencher on a triphosphate 125). During excitation, the light source 130 can provide excitation light 135 which is directed into substrate 105 so that total internal reflection TIR occurs at the substrate 105/coating 110 or substrate 105/fluid 120 interface. When the light 135 is internally reflected, a thin evanescent wave 140 is created in the lower index layer, i.e., in the exclusion coating 110.

FIG. 1B depicts a cross-section of one hole in the excitation zone 145 in accordance with another embodiment. As shown, in FIG. 1B, the excitation wave 140 is created from the TIR of the excitation light 135. The intensity of the evanescent wave 140 drops exponentially towards zero away from the surface so region 145 represents a zone of significant energy near the substrate 105 at the bottom of the hole 115. TIR can also be used to reflect the light off the non-sample side of the substrate to reuse the excitation light 135. The evanescent wave 140 can cause molecules in the analyte fluid sample 120 that are near the substrate to fluoresce, e.g., molecule 150. The small excitation zone 145 is the area that is both efficiently excited by the evanescent wave 140 and in fluidic contact with the sample 120.

FIG. 2 illustrates a top view (i.e., fluid side view) of a section of the excitation device 100 shown in FIG. 1A. As shown in FIG. 2, the exclusion coating 110 can cover the substrate (not shown) except for the holes 115. Fluorescent molecules that migrate into the bottom of the hole 115 can enter the excitation zone 145 (see FIG. 1B) and emit fluorescent light 115A.

FIG. 3A illustrates a side view of an excitation device 300 in accordance with an embodiment. As shown in FIG. 3A, the excitation device 300 is similar to excitation device 100. The excitation device 300 can include a substrate 305 and an exclusion coating 310 with holes 315. The excitation device 300 may be in contact with an analyte fluid sample 320, which can include fluorescently labeled nucleotide with a non-fluorescent quencher on the triphosphates 325. Substrate 305, exclusion coating 310, holes 315, and analyte fluid sample 320 have similar or identical properties/characteristics to the respective components of the excitation device 100.

The excitation device 300 can include a light guide layer 330. The light guiding layer 330 can be implemented using high-index of refraction materials as previously described. Light 340 from a light source 335 can be coupled into the light guiding layer 330 though a prism or grating as described in U.S. Pat. No. 5,882,472, which is hereby incorporated by reference in its entirety.

During excitation, the light source 335 can provide light 340 which is directed into the light guiding layer 330 so that total internal reflection TIR occurs at the light guiding layer 330/exclusion coating 310 and light guiding layer 330/fluid 320 interfaces. When light is internally reflected, a thin evanescent wave 345 is created in the lower index of refraction layer, i.e., in the exclusion coating 310 and in the fluid. The evanescent wave can cause molecules in the analyte fluid sample 320 that are near the light guiding layer 330 to fluoresce, e.g., molecule 355.

FIG. 3B depicts a cross-section of one hole in the evanescent wave 345 in accordance with another embodiment. As shown, in FIG. 3B, the evanescent wave 345 is created from the TIR of the excitation light 340 in the light guiding layer 330. The intensity of the evanescent wave 345 drops exponentially towards zero moving away from the boundary so region 350 represents a zone of significant energy near the light guiding layer 330 at the bottom of hole 315. TIR can also be used to reflect the light off the non-sample side of the light guiding layer 330 to reuse the excitation light 340. The evanescent wave 345 can cause molecules in the analyte fluid sample 320 that are near the light guiding layer 330 to fluoresce, e.g., molecule 355. The small excitation zone 350 is the areas that are both excited by the evanescent wave 345 and in fluidic contact with the sample 320.

Figure 4:
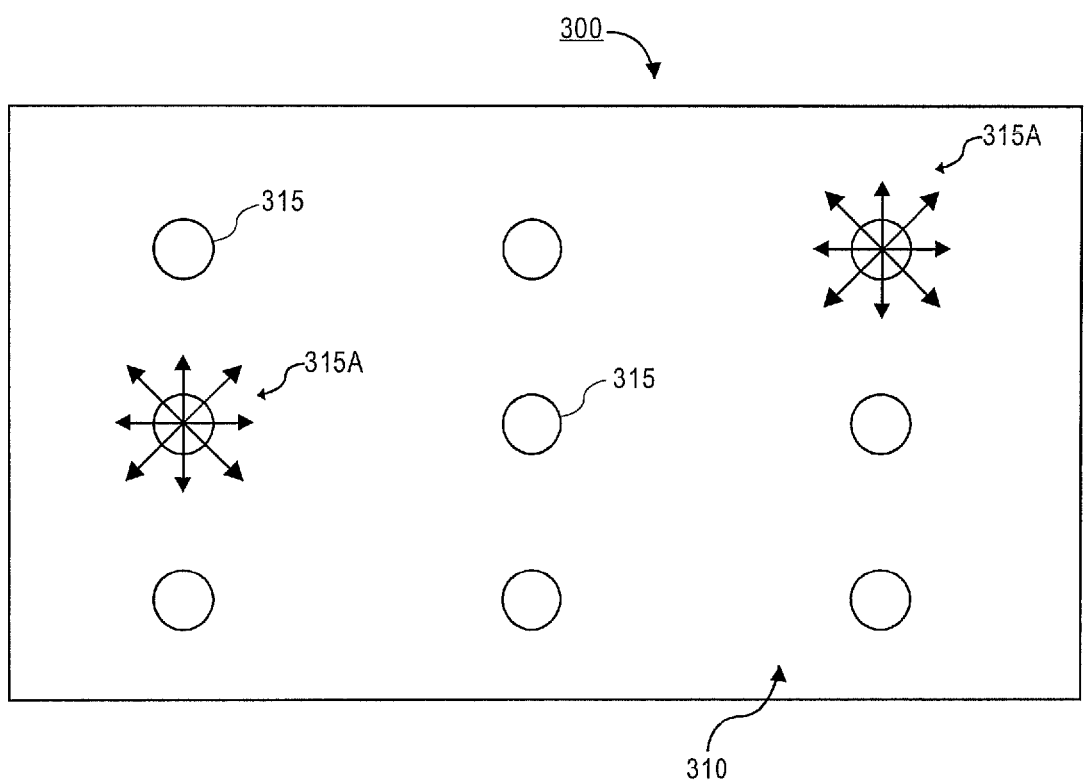
FIG. 4 illustrates a top view of the excitation device shown in FIG. 3A in accordance with yet another embodiment.

FIG. 4 illustrates a top view of the excitation device 300 shown in FIG. 3A in accordance with yet another embodiment. As shown in FIG. 4, the exclusion coating 310 can cover the light guiding layer 330 (not shown) except for the holes 315. Fluorescent molecules that migrate to the bottom of the hole 315 can enter the excitation zone 350 (see FIG. 3B) and emit fluorescent light 315A.

Figure 5A:
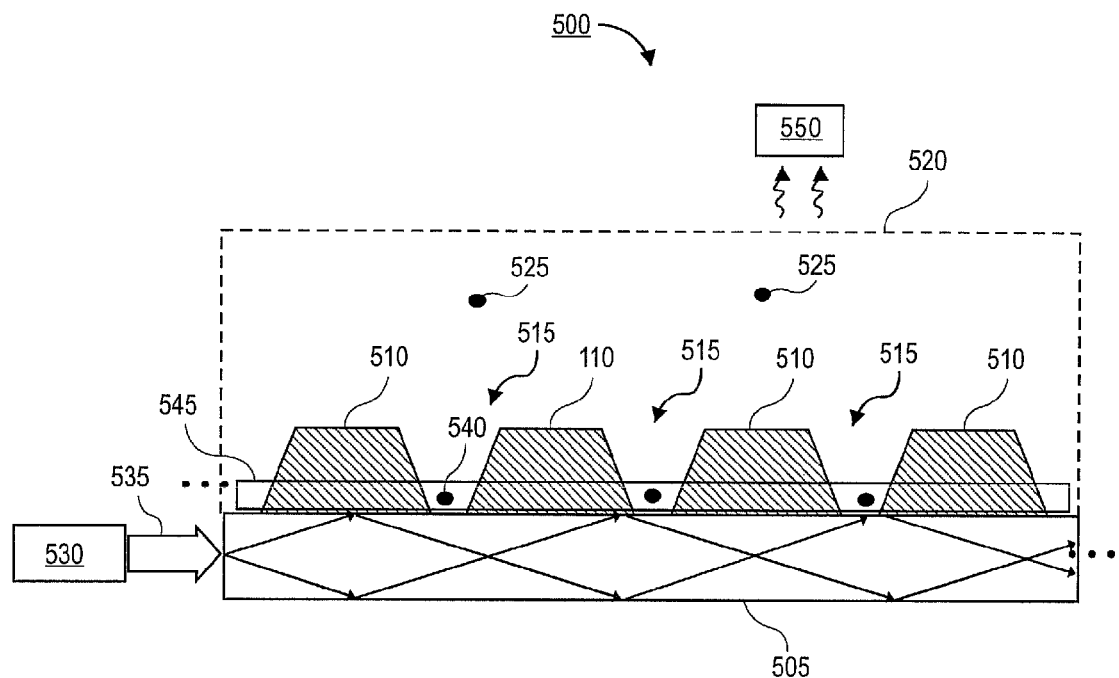
FIG. 5A illustrates a quantum excitation device in accordance with yet another embodiment.

FIG. 5A illustrates a quantum excitation device 500 in accordance with yet another embodiment. As shown in FIG.

5A, the quantum excitation device 500 is similar to excitation device 100. The quantum excitation device 500 can include a substrate 505 and an exclusion coating 510 with holes 515. The substrate 505 and the exclusion coating 510 can be implemented with the materials as previously described with respect to FIGS. 1A-4. Moreover, the index of refraction of the exclusion coating 510 is less than the substrate 505.

The quantum excitation device 500 can be in contact with an analyte fluid sample 520, which can also include fluorescently labeled nucleotide with a non fluorescent quencher on the triphosphates 525. Substrate 505, exclusion coating 510, holes 515, and analyte fluid sample 520 have similar and/or identical properties/characteristics to the respective components of the excitation device 100. The quantum excitation device 500 can also include a light source 530. Light 535 from the light source 530 can be coupled into the substrate 505. Similar to excitation device 300 (see FIG. 3AB), excitation device 500 can be implemented with a light-guiding layer similar to the light-guiding layer 330 in other embodiments.

Quantum excitation device 500 can include at least one quantum dot 540. A quantum dot can be a semiconductor nanostructure that confines the motion of conduction band electrons, valence band holes or excitons (bound pairs of conduction band electrons and valence band holes) in all three spatial directions. Quantum dots can include those made of silicon and germanium, and presumably of other materials, as well as CdSe. Quantum dots can also be fabricated as core-shell structures with, e.g., CdSe in the core and ZnS in the shell. It should be readily obvious that other types of materials could be used to create quantum dots and fall within the spirit and scope of the claimed invention.

Figure 5B:
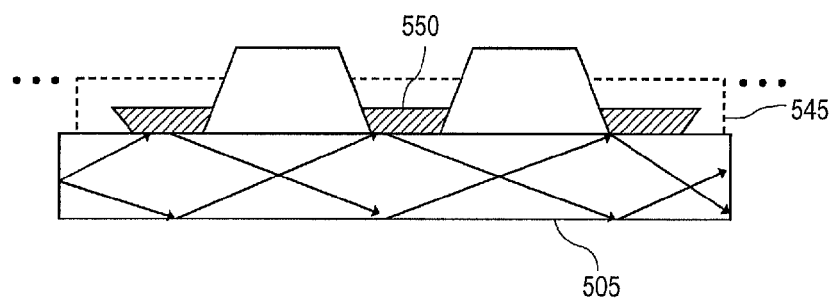
FIG. 5B illustrates a more detailed view of an excitation zone in the excitation device shown in FIG. 5A.

Other embodiments can use multiple quantum dots of differing size and/or types. During the excitation phase, the quantum dot 540 can create an energy transfer zone. More particularly, the light source 530 can provide light 535 which is directed into the substrate 505 so that TIR occurs at the substrate 505/exclusion coating 510 and at the substrate 505/fluid 520 interface. When the light 535 is internally reflected, a thin evanescent wave 545 is created in the lower index of refraction layer, i.e., in the exclusion coating 510. The evanescent wave 545 can create a small excitation zone 550 (see FIG. 5B) due to the rapid decay of the evanescent wave 545. The quantum dot 540 can absorb the energy in the small excitation zone 550 which converts the excitation energy into the desired wavelength. The conversion process can create an energy transfer zone surrounding the quantum dot 540, which is depicted in FIG. 6A.

Figure 6A:
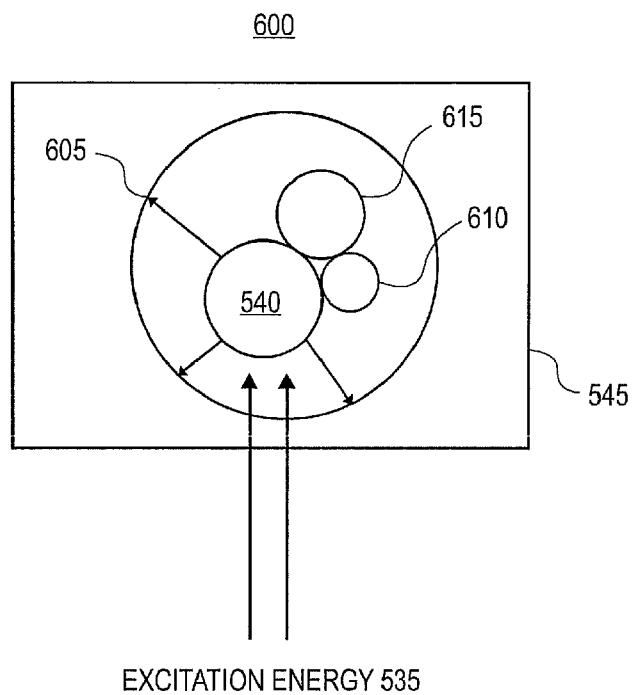
FIG. 6A depicts an energy transfer zone around a quantum dot.

As shown in FIG. 6A, the energy in the transfer zone 605 can be transferred to a labeled moiety, that is, an excited dye-labeled nucleotide 610. The dye-labeled nucleotide 610 can be attached to the quantum dot 540 by an enzyme 615. In some embodiments, multiple quantum dots of differing types and/or sizes can be used to have several excitation wavelengths, which are illustrated in FIG. 6B.

Figure 6B:
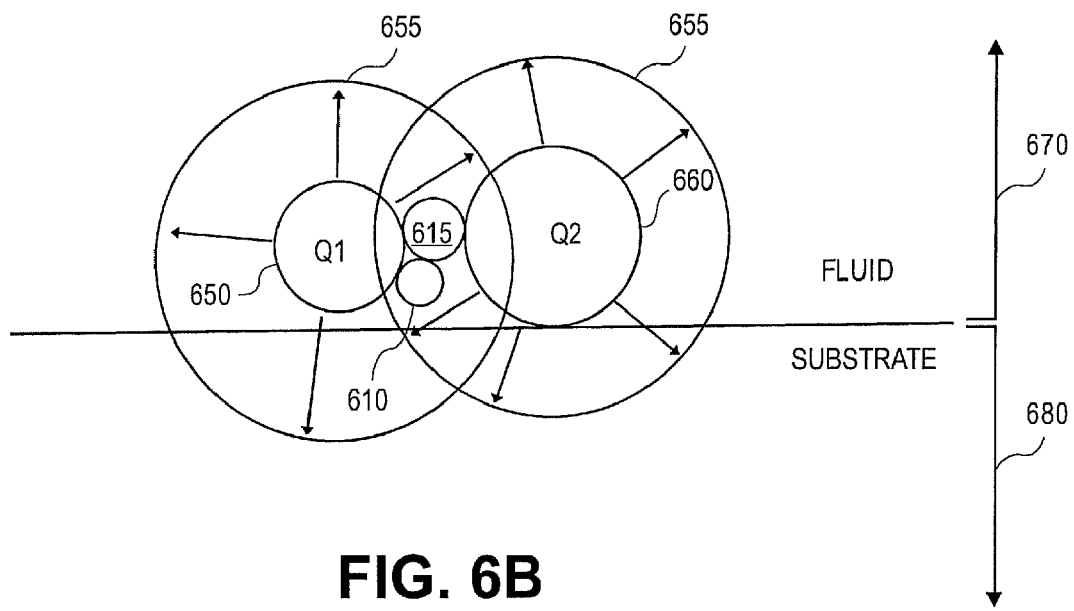
FIG. 6B illustrates an exemplary embodiment of multiple quantum dots.

As shown in FIG. 6B, quantum dot one (labeled as "Q1") 650 may create a surrounding energy transfer zone 655. Quantum dot two (labeled as "Q2") 660 may also create a surrounding energy transfer zone 665. The energy zones 655, 665 may be created by the presence of excitation energy. Since the quantum dots, 650 and 660, are of differing size, and may be of a differing type, they can both be used to generate several wavelengths. Like the embodiment shown in FIG. 6A, a dye labeled nucleotide 610 can be attached to the quantum dots 650, 660 by at least one enzyme 615.

Returning to FIG. 5A, the quantum excitation device also includes a detector 550, which is configured to identify the type of emission from the quantum dots. The detected emission is then directed to a computer (not shown) where the molecule corresponding to the emission is identified and its identity stored.

Figure 7A:
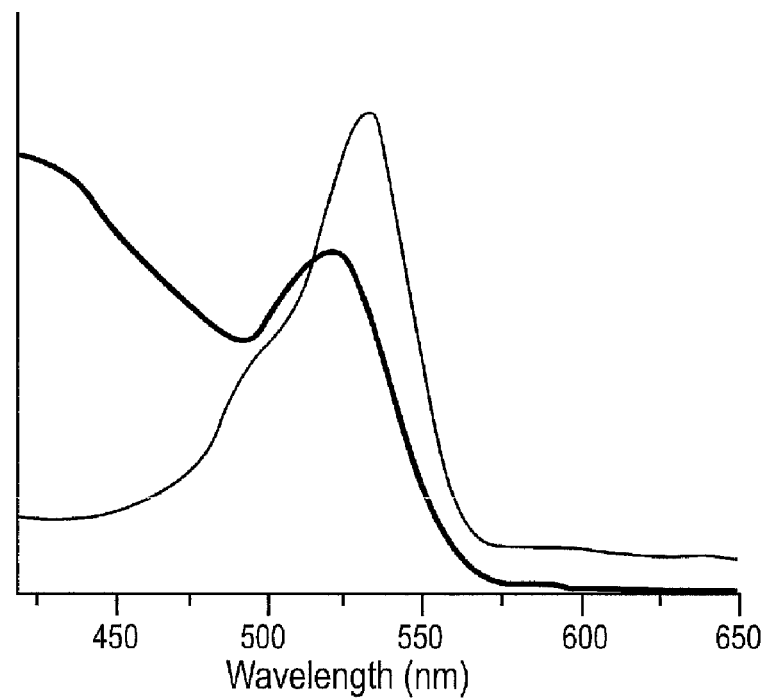
FIG. 7 depicts a comparison of Rhodamine 6G and quantum dyes by emission and excitation profiles.
Figure 7B:
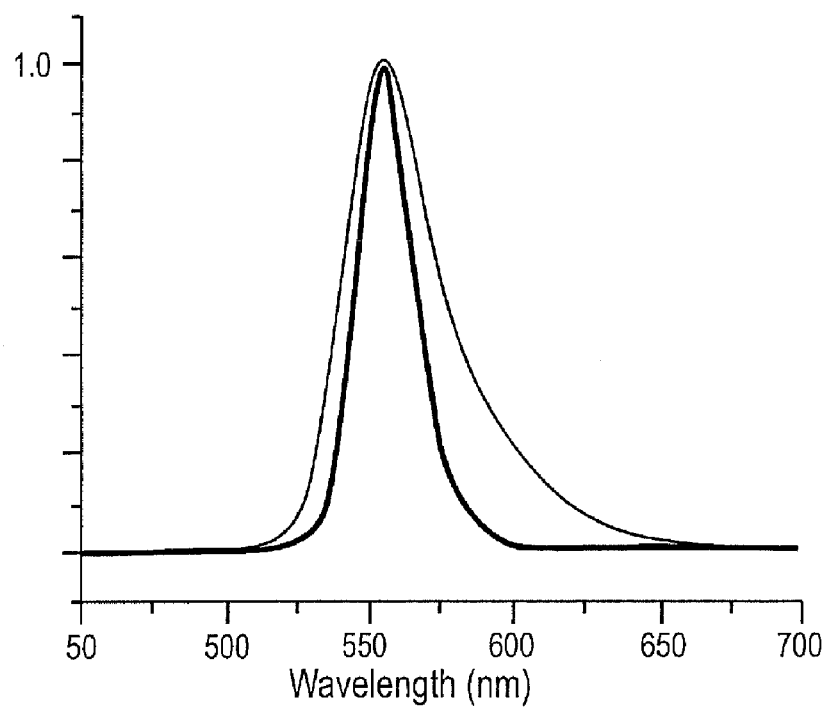

FIG. 7 depicts a comparison 700 of (a) the excitation and (b) emission profiles between CdSe quantum dots and Rhodamine 6G dye. The quantum dots emission spectrum (in (b)) is nearly symmetric and narrower in peak width. However, its excitation profile is broad and continuous. Thus, the quantum dots can be efficiently excited by wavelengths shorter than 530 nm. By contrast, the organic dye Rhodamine 6G has excitation peaks which limit excitation wavelength choices.

Figure 8:
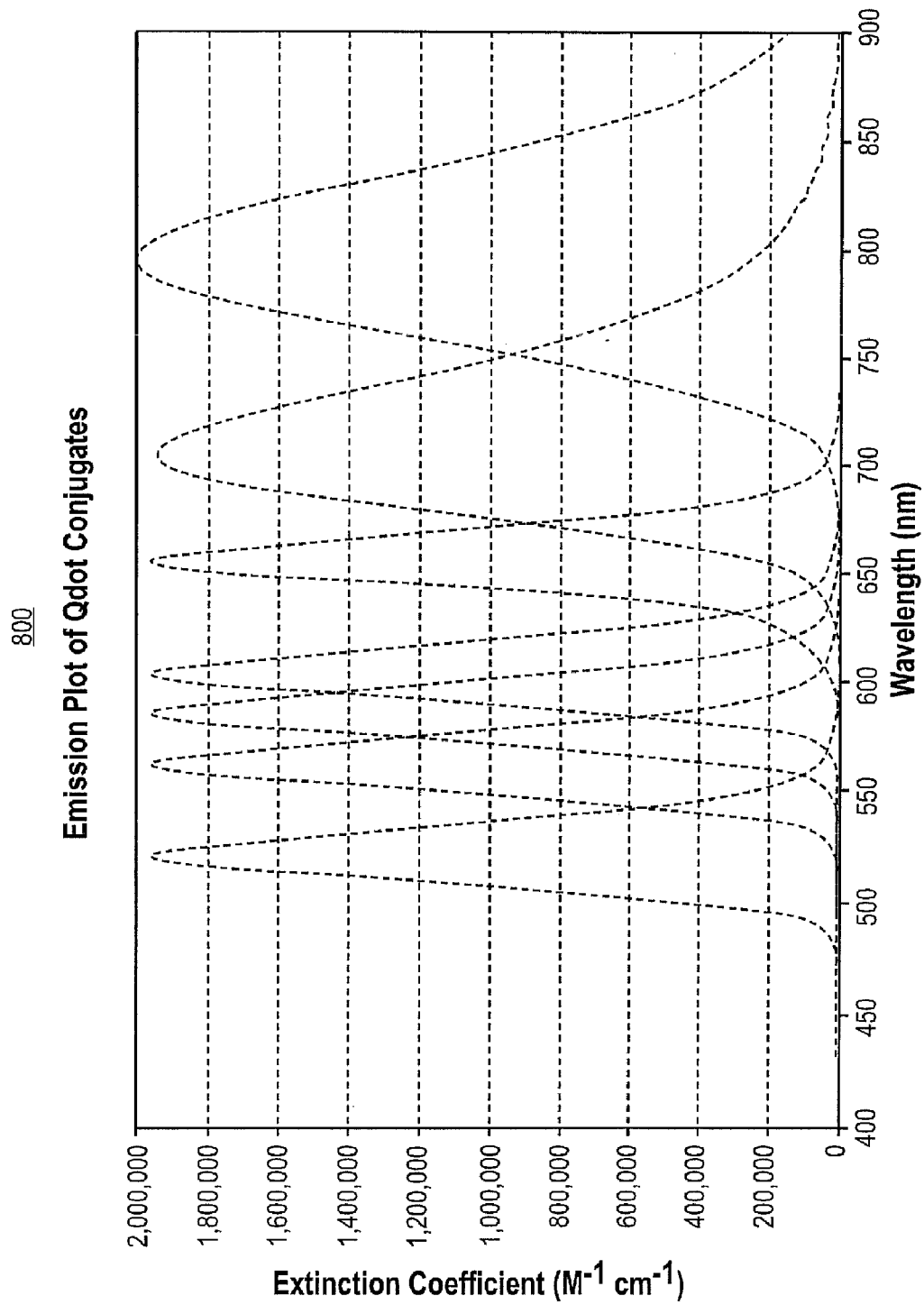
FIG. 8 depicts emission profiles for some commercially available quantum dots.

FIG. 8 depicts emission profiles 800 for some commercially available quantum dots. As shown in FIG. 8, the wavelength spread from commercially available samples can be considered reasonable. Accordingly, it is anticipated that careful selection and/or fabrication can enable even tighter distributions.

Returning to FIG. 6A, quantum dot 540 is depicted attached to the dye labeled nucleotide 610 and enzyme 615. Ideally, a single enzyme 615 is attached to a single quantum dot 540 and the attached pair is then attached to the substrate 505. In the quantum excitation device 500, it is further desired to have a single moiety in each excitation zone. The odds of getting one and only one of each moiety and attached pair in a well are low if standard Poisson distributions are created. At best, it would by $0.37^2$ (14 percent) but typically something in the 10 percent is more likely. This low useful density can decrease the effective throughput of a system.

One conventional strategy is to enrich the number of correct pairs. For example, one solution is to perform attachment chemistry using dilute solutions such that most molecules are not part of a pair. Because of the low concentrations, there are few moieties with more than one of each. This solution can then be enriched by selection (such as using a Fluorescent Activated Cell Sort instrument) or by pullout using a chemical hook such as Streptavidin-Biotin, which is known to those skilled in the art.

Figure 9:
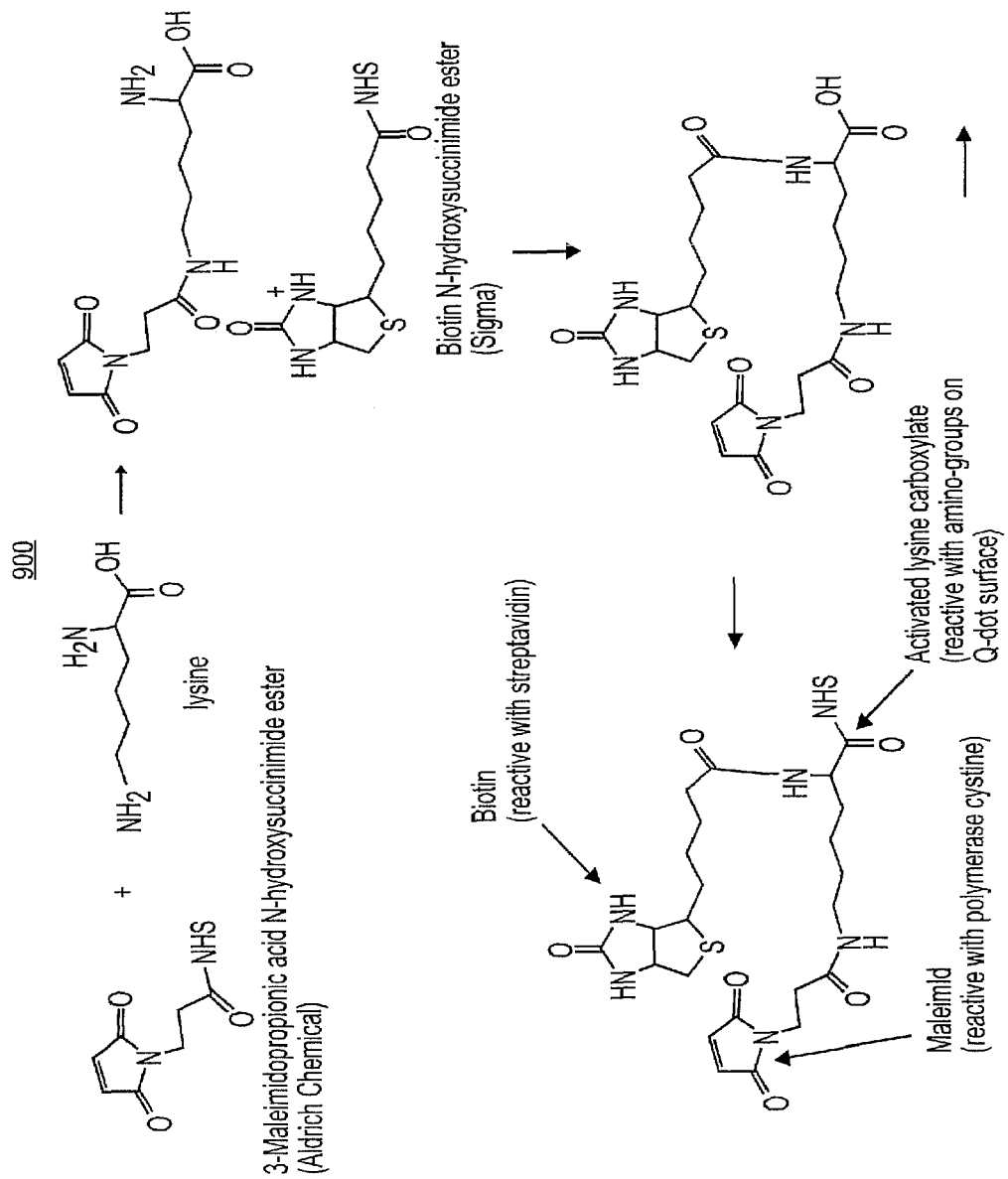
FIG. 9 depicts the process for a tri-functional reagent for surface attachment to quantum dots.
Figure 10:
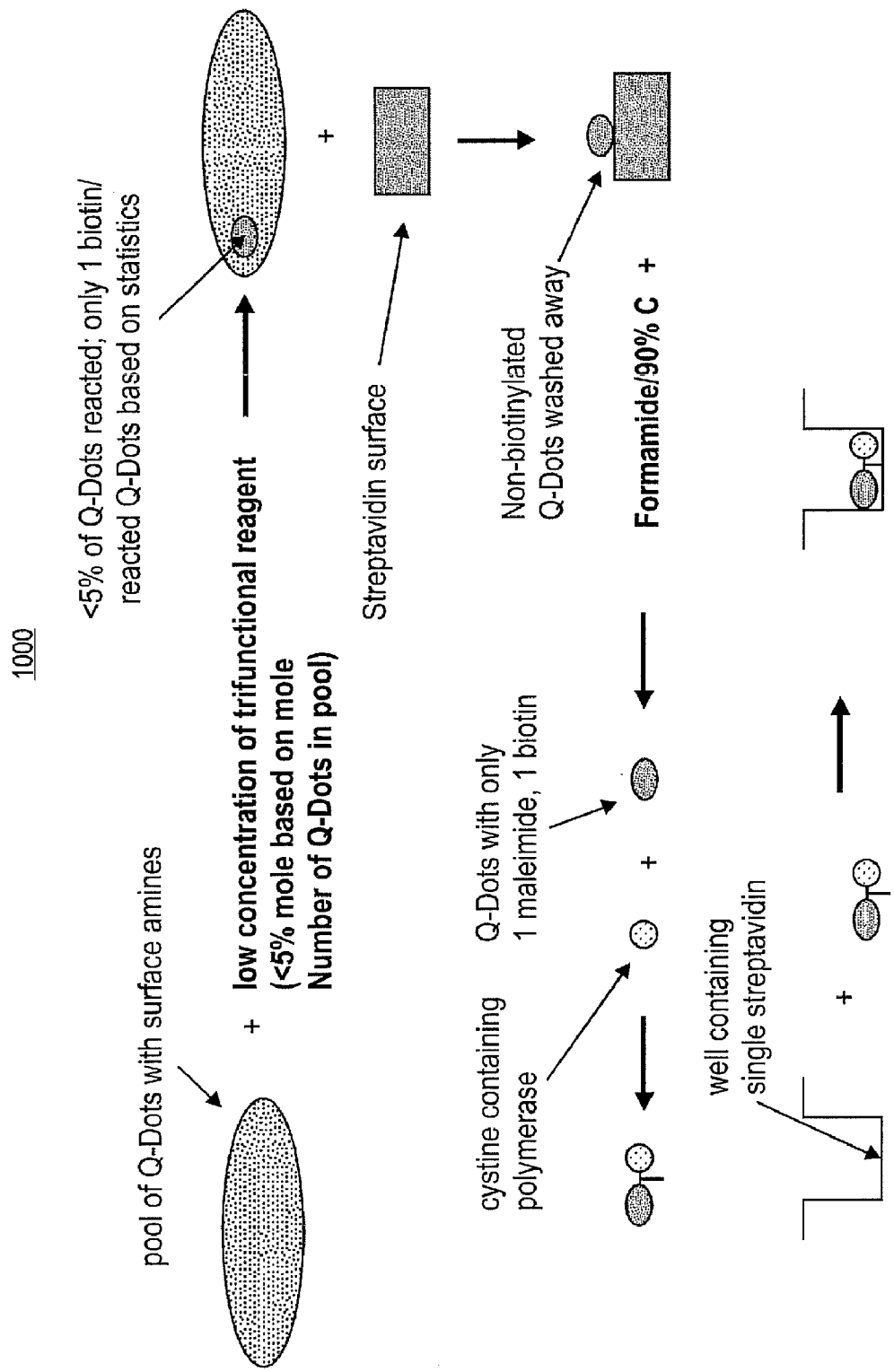
FIG. 10 depicts the process of synthesis of quantum dots containing single polymerase, single biotin.

Embodiments of the quantum excitation device can use a linker molecule that has three attachment sites. FIG. 9 depicts the process 900 for a tri-functional reagent for surface attachment to quantum dots 540. FIG. 10 depicts the process 1000 of synthesis of quantum dots 540 containing single polymerase, single biotin.

Through the processes of FIGS. 9-10, an enzyme containing at least one Cystine can be attached to each maleimide containing quantum dot by driving the reaction to completion. Thus, each quantum dot that has a single hook biotin attached will have a single enzyme. This can be attached to the substrate 505. In other embodiments, the well can include multiple streptavidins, as described in U.S. Provisional Application 60/689,692, filed on Jun. 10, 2005, entitled "Method and System for Multiplex Genetic Analysis," which is hereby incorporated by reference in its entirety.

Accordingly, embodiments of the quantum excitation device can provide some advantages over the conventional systems. For example, the quantum dots in the excitation device can provide multiple methods of attenuation in a single system. Another advantage is that evanescent layer of excitation is approximately 100 nm thick using TIR. This reduces the excitation zone by limiting excitation light in the Z-axis. Moreover, the excitation source can be at a wavelength that weakly excites the moiety of interest. For example, a wavelength of 405 nm would weakly excite the Rhodamine 6G-dye shown in FIG. 7, but the quantum dots are well excited at these shorter wavelengths. This wide absorption range also permits the use of different excitation sources. For example, 405 nm lasers (used in high definition DVD players) are much cheaper than a 488 nm laser used in conventional fluorescent excitation.

Yet another advantage of the embodiments is that quantum dots or other long life donors create a second excitation zone. This limits the number of sources in the all directions. Incorporated or bound nucleotides see high levels of efficiently absorbed light only if they are very near the quantum dot. The effective energy transfer distances are on the order of 5 nm so this creates small scale excitation zones.

Yet another advantage is free nucleotides that diffuse into the energy transfer zone (see 605 in FIG. 6A) will typically exit very rapidly due to the extremely small excitation volume. The time for free nucleotides to diffuse in and out of the energy transfer zone is much shorter than that for an enzyme to incorporate a nucleotide. This improves moiety determination based on accumulated signal (for example via CCD detection) as opposed to a single photon counting.

Another embodiment using two-photon excitation can be used to reduce background noise. With two-photon excitation, the emission of light is at shorter wavelength than the excitation light. Two-photon emission is only generated where a high excitation level exists. Any background fluorescence is at longer wavelength than the excitation source and is easily filtered out using filters such as short pass or band-pass filters.

Another embodiment can use an alternative to TIR. These embodiments use surface plasmon-coupled direction emission ("SPCE"). SPCE can include using angular emission profiles of dye molecules excited by surface plasmon waves at a metal surface, which is described in WO 2005/003743. The entirety of WO 2005/003743 is incorporated by reference. SPCE techniques can be combined with the embodiments of the excitation device described previously to provide improved excitation and collection with zeptoliter excitation volumes, which are depicted in FIG. 11A-D.

Figure 11A:
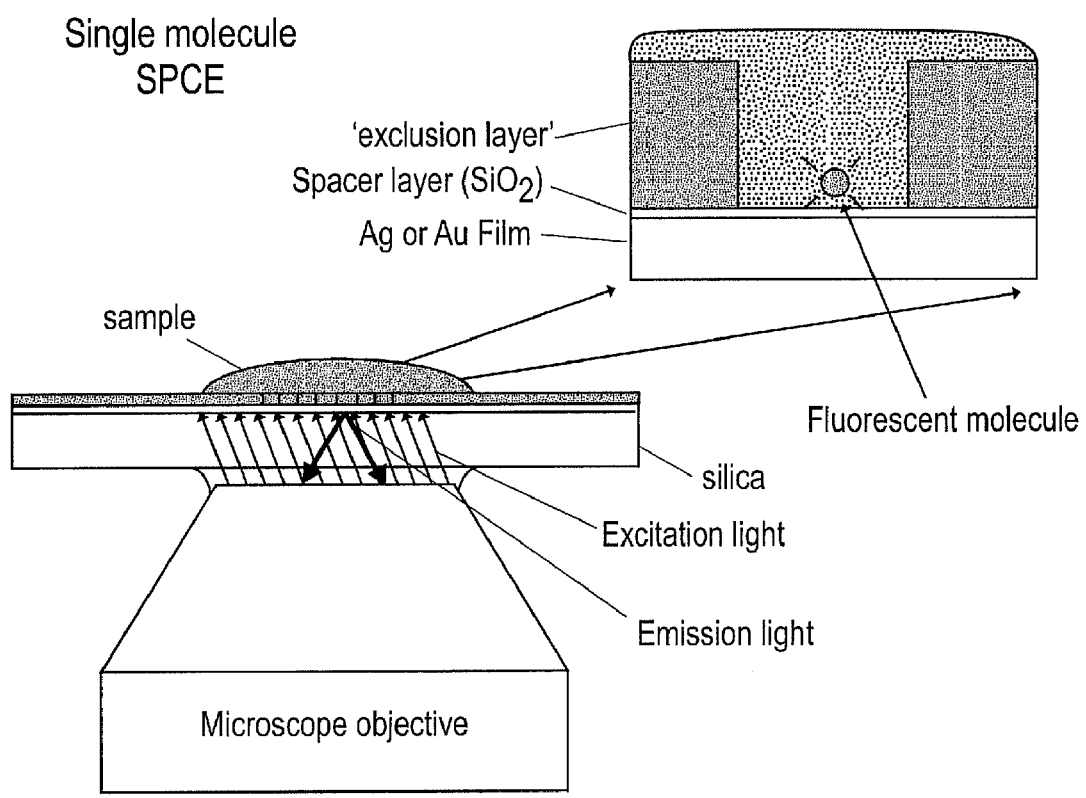
FIG. 11A depicts a Kretschmann configuration in accordance with yet another embodiment.

FIG. 11A illustrates an exemplary embodiment of a Kretschmann configuration system 110A. In this configuration, energy from the fluorescent molecule is emitted as light on the other side of the metal surface. Background can be suppressed and both excitation and emission efficiencies can be significantly improved. If the fluorescent molecule is too close to the metal surface (<20 nm) than the energy is quenched. A spacer layer can be used to prevent such intimate contact. The spacer layer can be dielectric material with a low fluorescence such as $SiO_2$.

SPCE techniques can offer some advantages over TIR systems. For example, the choices for the exclusion coating are larger because the evanescent wave is not created by the transition to a low index material. In addition, the directional nature of the emitted light can simplify the collection optics and improve background rejection. Finally, the proximity to metal has been shown to increase photo stability, which is especially important for single molecule applications.

Figure 11B:
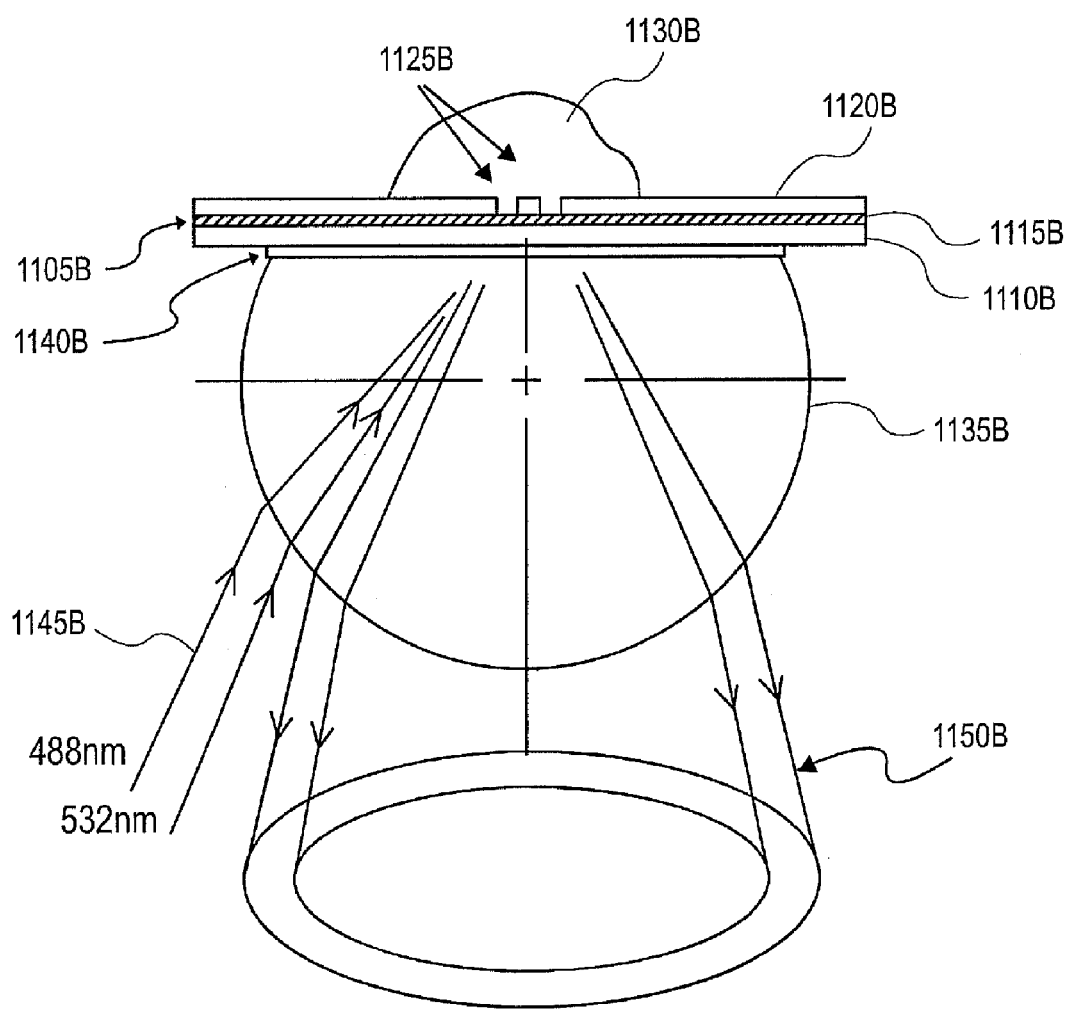
FIG. 11B illustrates another SPCE system in accordance with yet another embodiment.

FIG. 11B illustrates another embodiment of a SPCE system 1100B. As shown in FIG. 11B, an excitation device can include a substrate 1110B interfaced with a metal layer 1115B, and an exclusion coating 1120B. The substrate 1110B and the exclusion coating 1120B can be implemented with materials and techniques as described earlier. The metal layer 1115B can be implemented with gold, silver or other metals appropriate for SPCE with a thickness of 5-75 nm or more, preferably 25-30 nm for gold, and 50 nm for silver. In addition, another metal such as chromium may be applied to the substrate in order to improve adhesion while not interfering with the refractive index of the thicker layer which is subsequently applied; this layer has been reported to be between 2 to 5 nm. In some embodiments, the metal layer 1115B can be a non-metallic material that has a significant change in index from the substrate 1110B.

The exclusion coating 1120B can be deposited or grown on one side of the metal layer 1115B. The exclusion coating 1120B can be implemented with high-index of refraction material (e.g., fused silica, polycarbonate) as previously described with respect to FIGS. 1A-4. Holes (channels, slots, etc.) 1125B can be formed in the exclusion coating 1120B for the analyte solution 1130B to contact with the metal layer 1115B. Like some other embodiments, dye molecules (e.g., labeled nucleotides) can migrate to the bottom of the hole 1125B.

The SPCE system 1100B can also include a lens 1135B implemented as a truncated sphere, hemisphere or other similar three dimensional shape. The lens 1135B can be configured to be in an aplanatic condition, that is, the lens 1135B doesn't create spherical aberrations or coma. The lens 1135B can be configured to interface with the substrate 1110B through an index matching fluid 1140B which can couple light in, and out at the steep angles required. In some embodiments, the excitation source 1145B can operate at a single frequency or, in the case of this embodiment, multiple frequencies such as 488 nm and 532 nm.

Accordingly, when the light from the excitation sources 1145B hits the substrate 1110B, a surface plasmon is excited at the interface of the metal layer 1115B and the substrate 1110B. The surface plasmon can be considered as a ray of light bound onto a surface of the metal layer 1115B propagating along the surface and presenting itself as an electric field. The electric field extends into the exclusion layer 1120B and the holes 1125B and rapidly decays with distance from the metal surface. Prior to the decay of the electric field, an energy transfer zone can be created similar to the zone of significant energy 145 of FIG. 1B. The dye molecules (e.g., labeled nucleotides) that have migrated into this energy transfer zone can be energized and fluoresce and much of the energy can be emitted by plasmon coupled emission which forms a cone of emission light 1150B.

Figure 11C:
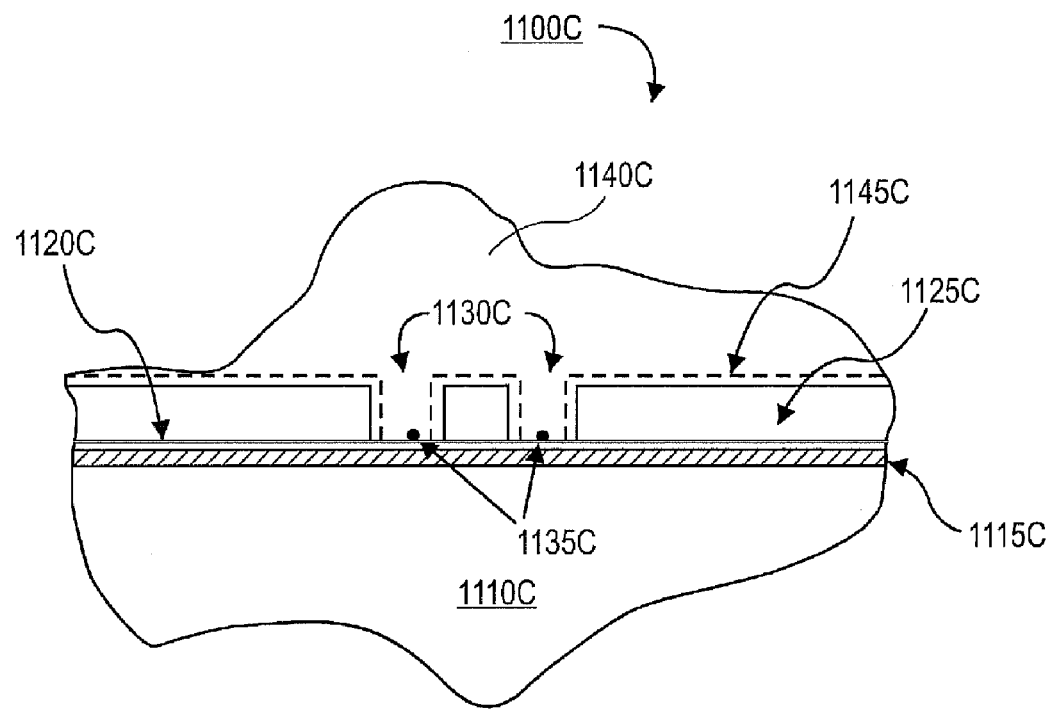
FIG. 11C illustrates yet another SPCE system in accordance with yet another embodiment.

In some embodiments of 1100B, the exclusion coating 1120B can be implemented with material that does not support total internal reflection, i.e equal or higher index than the substrate, i.e., not matching with index matching fluid 1140B. The coating can be lower but doesn't have to be because TIR does not occur. In other embodiments, the exclusion coating 1120B can be implemented with materials with a lesser index of refraction. The material can be a metal or a non-transparent material as known to those skilled in the art FIG. 11C illustrates another exemplary SPCE system 1100C in accordance with yet another embodiment. As shown in FIG. 11C, the system 1100C includes an excitation device. The excitation device can include a substrate 1110C, which can be implemented with similar materials as described earlier with respect to FIG. 1A and FIG. 3A. The substrate 1110C can be in contact with a metal layer 1115C. The metal layer 1115C can be implemented with materials similar to the metal layer 1115B of FIG. 11B as described herein above. In some embodiments, the metal layer 1115C can be a non-metallic material that has a significant change in index from the substrate 1110C. The metal layer 1115C and substrate 1110C interface can be used for SPCE excitation.

A spacer layer 1120C can be formed on one side of the metal layer 1115C. The spacer layer 1120C can be implemented with $SiO_2$ in a range of 1-100 nm and preferably 5-25 nm thick. A metal coating 1125C can be formed on one side of the spacer layer 1120C. The metal coating 1125C can be implemented with material such as gold, aluminum, titanium or other similar materials. Holes 1130C can be formed within the metal coating 1125C, where dye molecules (e.g., labeled nucleotides) 1135C in a fluid 1140C can migrate to the bottom of the holes 1130C.

Accordingly, when the light from an excitation source substrate 1110C, a surface plasmon is excited at the interface of the metal layer 1115C and the substrate 1110C. The surface plasmon can create an electromagnetic field that extends into the holes 1130C that rapidly decays. An energy transfer zone can be created similar to the zone of significant energy 145 of FIG. 1B. The labeled nucleotides 1135C that have migrated into this energy transfer zone can be energized and fluoresce.

Moreover, a zone of quenching 1145C can be created due to the interaction of the dyes with the thick metal coating 1125C. The zone of quenching 1145C can be approximately 20 nm. Any dye molecules in this zone are suppressed from fluorescing.

Figure 11F:
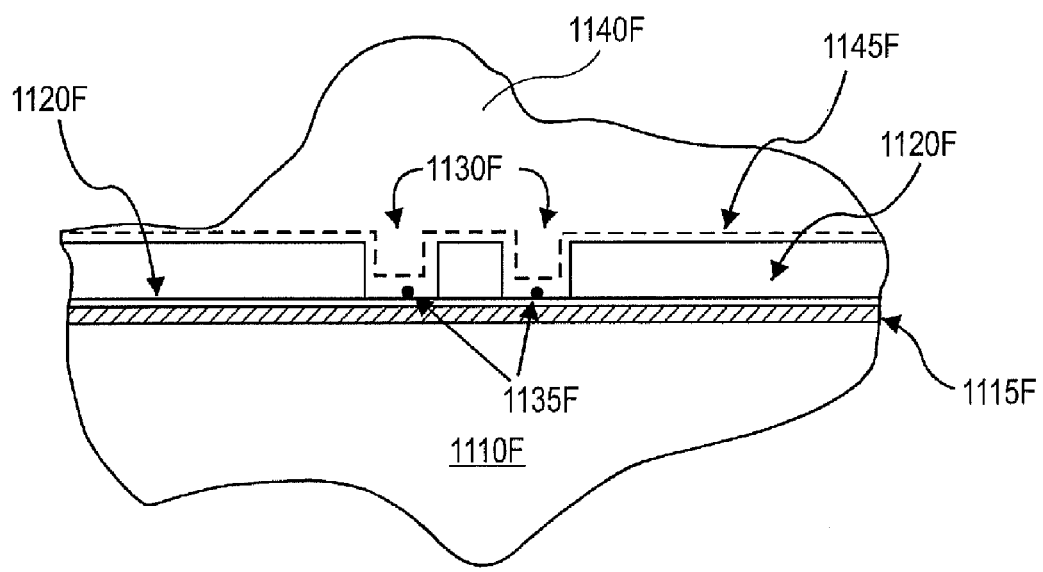
FIG. 11F illustrates yet another exemplary SPCE system in accordance with yet another embodiment.
Figure 11D:
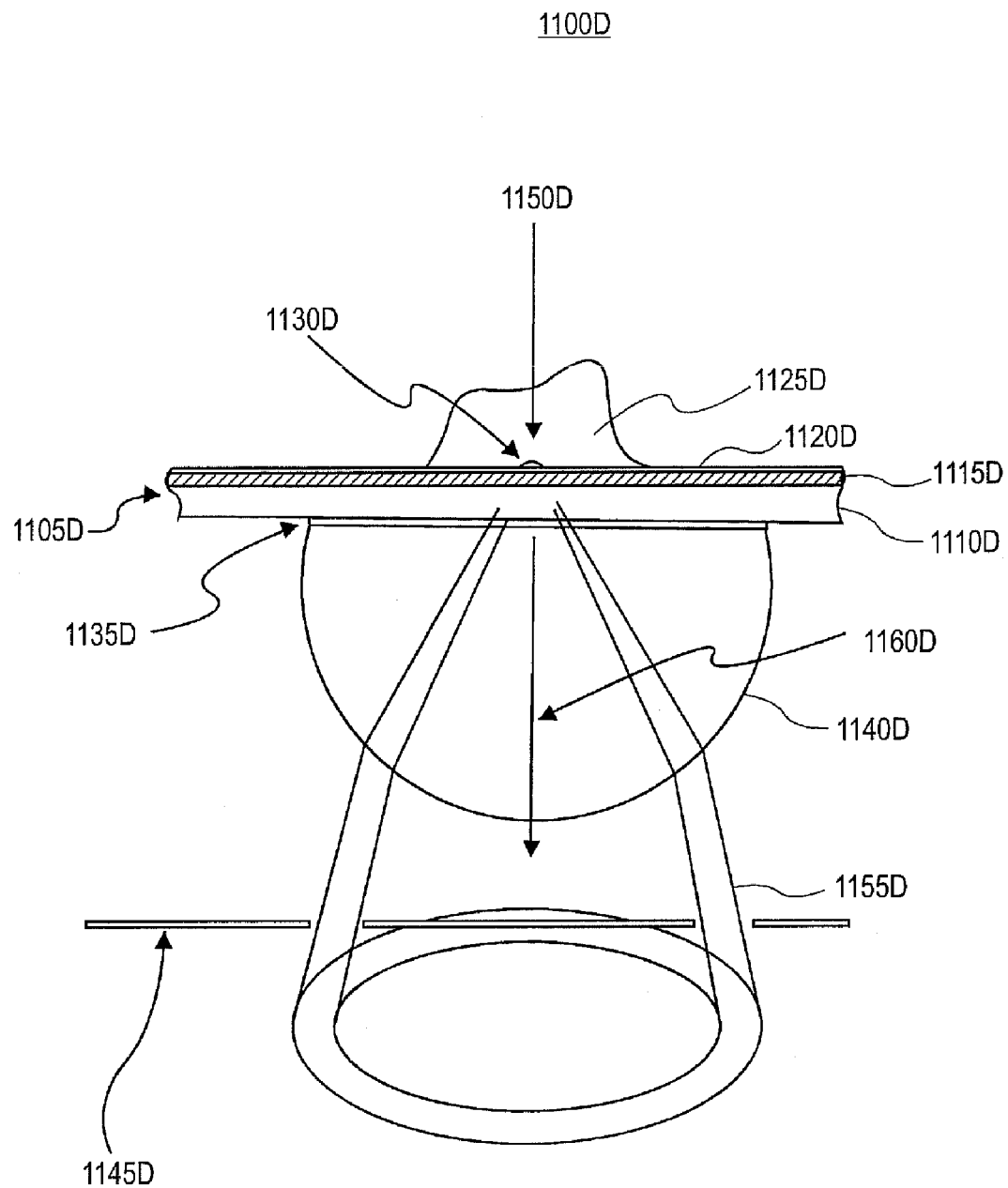
FIG. 11D illustrates a reverse Kretschmann system in accordance with yet another embodiment.

FIG. 11D illustrates a reverse Kretschmann excitation system 1100D for SPCE. As background, reverse Kretschmann ("RK") is a conventional approach for SPCE. In RK, the excitation is from the sample side but the emission is on the other side of the metal surface. When excitation light is brought in on the sample side, it excites dye molecules along the way. There are many dye molecules away from the surface and some of the emitted light will transmit through the metal surface since the metal is not thick enough to block all the light. This will cause too high a background. Moreover, the excitation light can bleach the samples before they get near the surface. The embodiment shown in FIG. 11D can solve these issues.

As shown in FIG. 11D, the excitation system 1100D can include an excitation device 1105D, which can include a substrate 1110D interfaced with a metal layer 1115D, and a spacer layer 1120D. The substrate 1110D, metal layer 115D and spacer layer 1120D can be implemented with materials and techniques as described earlier with respect to FIGS. 11A-C. In some embodiments, the metal layer 1115D can be a non-metallic material that has a significant change in index from the substrate 1110D. The spacer layer 1120D can be in contact with an analyte solution 1125D. Quantum dots 1130D can be bound to the spacer layer 1120D. For clarity, quantum dots are described but it is understood that other absorbers could be used such as noble metal nanodots (colloidal particles).

One side of the substrate 1110D can be in contact with an index matching fluid 1135D. A lens 1140D can encompass the index matching fluid 1135D on the substrate 1110D. The lens 1140D may be implemented as a truncated sphere, hemisphere or other similar three-dimensional shape. The lens 1140D can be configured to be in an aplanatic condition, that is, the lens 1140D avoids spherical aberrations. The lens 1140D may also be implemented as a reflective or catadioptric lens in general, and as a Schwarzschild objective in particular. While the hole required through the primary mirror of centered reflective systems and the obscuration due to the secondary mirror are limitations for many imaging systems, they are not limitations for a Kretschmann system. They are not limitations since the elicited luminescent is emitted into an annular pattern that is entirely collectible by a two mirror system, even though they comprise hole in the primary and an obscuration due to the secondary. Exemplary reflective 1190D and catadoptric 1195E lenses are shown in FIG. 11E. The system 1100D can also include an aperture 1145D, which is configured to block primary excitation background emissions, and plasmon emissions from the quantum dot 1130D from collection sensors (not shown).

Light beam 1150D (e.g., wavelength 405 nm, or 980 nm for up-converting phosphors) from an excitation source (not shown) can excite the quantum dots 1130D, which generate a small emission zone with a low background. Since the excitation light is spectrally far removed from the dye emission and absorbance, the excitation light beam 1150D can easily be optically filtered and the dyes poorly absorb the primary emission light, which reduces photo degradation of the dyes. The light emitted from the dyes near the colloidal particles 1130D can be emitted in a narrow angular distribution on the substrate 1110D side in a cone of light 1155D The cone of light 1155D can be efficiently collected and filtered and then detected by a sensor such as a charge coupled detector. Some of the excitation light beam 1160D can be transmitted to the substrate side 1110D but this light can be easily blocked, filtered or directed away from the collection area.

FIG. 11F illustrates another exemplary SPCE system 1100F in accordance with yet another embodiment. As shown in FIG. 11F, the system 1100F includes an excitation device. The excitation device can include a substrate 1110F, which can be implemented with similar materials as described earlier with respect to FIG. 1A and FIG. 3A. The substrate 1110F can be in contact with a thin metal layer 1115F. The metal layer 1115F can be implemented with materials similar to the metal layer 1115B of FIG. 11B as described herein above and with a thickness of about 25-50 nanometers. A second metal layer 1120F can deposited over the metal layer 1115F. The second metal layer 1120F can be a thickness of about 100 nm and implemented with materials similar to the metal layer 1115F or a different metal. The thickness of the second metal layer 1120F prevents coupling of any surface plasmons and reflects the surface plasmons. Accordingly, the metal layer 1115F and substrate 110F interface can be used for SPCE excitation. The first metal can be pure or an alloy provided plasmons are supported. The addition of the second layer should not support surface plasmons (i.e. it can be a thicker layer of same metal or it can be a different metal or alloy.

Holes 1130F can be formed within the second metal layer 1120F, where dye molecules (e.g., labeled nucleotides) 1135F in a fluid 1140F can migrate to the bottom of the holes 1130F. Holes can be any size where smaller holes allow higher concentrations for faster kinetics. Size can be less than 1000 nm preferably less than 200 nm and still more preferably less than 100 nm.

Accordingly, when the light from an excitation source substrate 1110F, a surface plasmon is excited at the interface of the metal layer 1115F and the substrate 1110F. The surface plasmon can create an electric field that extends into the holes 1130F that rapidly decays. The labeled nucleotides 1135F that have migrated into this energy transfer zone can be energized and fluoresce.

Moreover, a zone of quenching 1145F can be created due to the interaction of the dyes with the second metal layer 1120F. The zone of quenching 1145E can be approximately 20 nm. Any dye molecules in this zone are suppressed from fluorescing.

Figure 12:
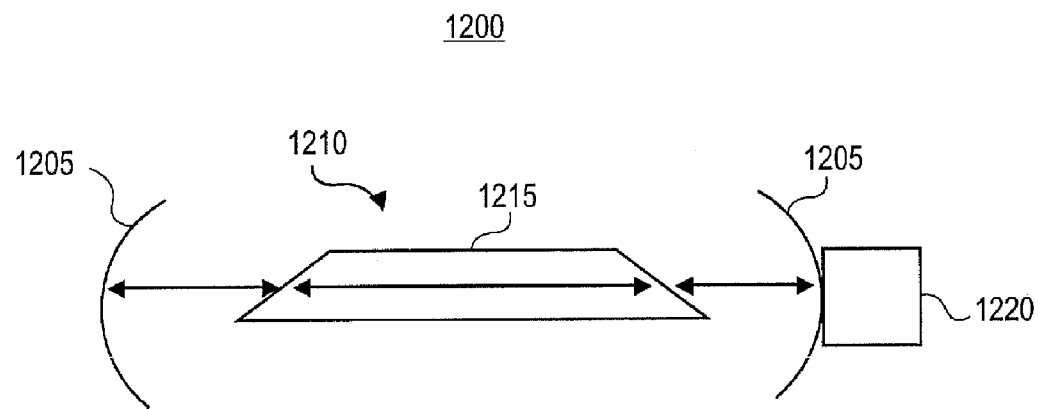
FIG. 12 depicts a conventional resonant laser cavity.

Returning to FIGS. 1A and 3A, the respective light sources (130 and 335) can be generally described as sources of excitation energy at a selected wavelength. In conventional systems, the light source may be a resonator cavity laser as depicted in FIG. 12. As shown in FIG. 12, a resonator cavity laser 1200 includes highly reflective mirrors 1205. Within the cavity 1210, a laser pump 1215, for example, an argon ion laser pump, may generate the selected wavelength, which is reflected between the mirrors 1205 until it can pass through the output coupler 1220.

Conventional resonator cavity lasers have drawbacks and disadvantages. For example, the laser power outside the resonator cavity laser is approximately 100 times less than inside the resonator cavity. Accordingly, additional embodiments generally pertain to increasing fluorescence generation. More particularly, embodiments can enhance optical processes by placing fluorophores in communication with the resonator cavity so that they are exposed to an excitation field amplitude comparable to that existing within the cavity rather than that of a beam substantially outside the cavity. In other embodiments, an efficient use of laser power can be exciting fluorophores located in holes of the embodiments of the excitation devices implemented with an exclusion coatings or metallic coatings comprising holes with dimension and pitch less than the wavelength of the laser on silica substrate by using the excitation device 1320 as a cavity mirror, as depicted in FIG. 13.

Figure 13:
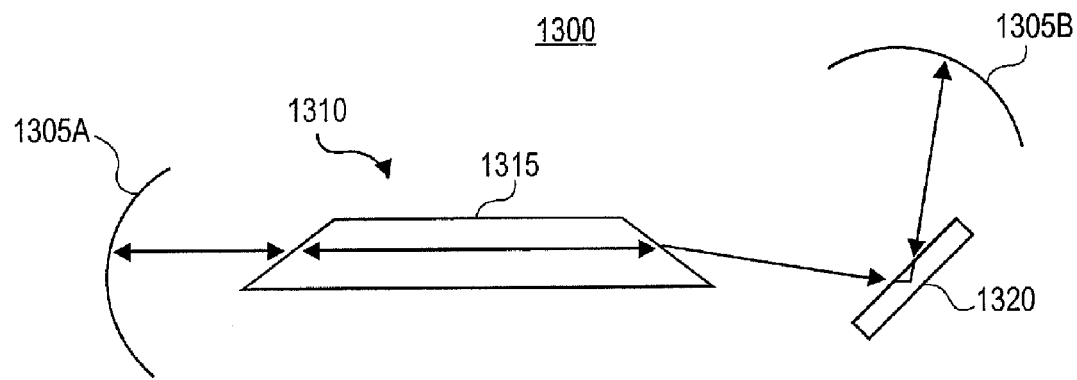
FIG. 13 illustrates a system in accordance with an embodiment of the invention.

FIG. 13 illustrates a system 1300 in accordance with an embodiment of the invention. As shown in FIG. 13, the system 1300 can include highly reflective mirrors 1305A and 1305B. A light source 1315 can be set up inside of a resonant cavity 1310. Positioned inside a laser resonant cavity can be the substrate 1320, e.g. Substrate 105 shown in FIG. 1. The substrate 105 should be configured to efficiently reflect the light, for example by TIR, at the exclusion layer interface such that the evanescent wave can excite the fluorophores that penetrate the holes in the exclusion layer while the resonant beam circulates within the cavity. Technically speaking, the fluorophores are outside the cavity since the TIR surface comprises one of the resonator boundaries. But there is an evanescent component of the intra-cavity beam that extends nanometers beyond the interface.

Figure 14:
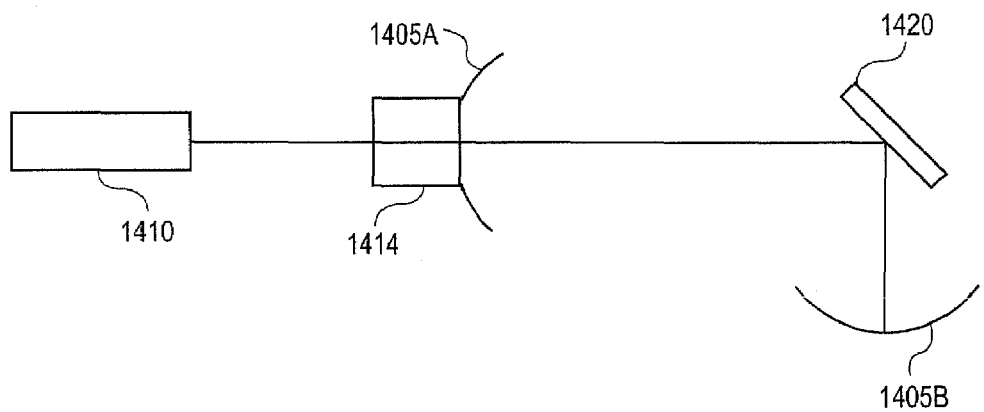
FIG. 14 illustrates a system in accordance with an embodiment of the invention.

FIG. 14 illustrates a system 1400 in accordance with an embodiment of the present invention. As shown in FIG. 14, system 1400 depicts excitation of the luminophores on the excitation device 1420 through an external laser 1410. The system 1400 can include highly reflective mirrors 1405. The external laser 1410 may generate coherent light energy at the selected frequency directed into the resonant cavity defined by mirrors 1405. An active cavity alignment device 1414 establishes and maintains the cavity length and alignment necessary for resonance. Resonance allows a high field to build up in the cavity. The substrate of the excitation device 1420 can be configured to efficiently interface with the resonant cavity such that the evanescent wave can excite the fluorescently labeled dNTPs that migrate into the holes in the exclusion coating. The path of the coherent light energy can reflect to the second highly reflective mirror 1405B and then be reflected back towards the excitation device 1420.

FIGS. 15A-D depict various embodiments of the resonator cavity excitation devices 1500. As shown in FIGS. 15 A-C, a substrate 1505 can be interfaced with an aqueous luminescent analyte 1510. The interface can constitute a TIR interface 1525. The resonator cavities of 1515 are bounded by the highly reflective mirrors 1520 and the TIR interface 1525. Light path 1530 represents the various angles of light beam into the substrates 1505. For the sake of clarity, the holes or wells have been omitted. It should be noted that wells may be omitted in the actual device and the devices depicted in FIGS. 15A-D would still function. For instance, one could pattern a hybridization array on the liquid side of the interface and use resonant cavity enhancement. In some embodiments, the substrate can mean at least one piece of refractive material. For the embodiments shown in FIGS. 15A-D, one piece of glass is depicted. Preferably, one would have a very thin layer of glass in optical contact with the prism or lens and have the fluid in contact with the other side of the thin layer.

Figure 15B:
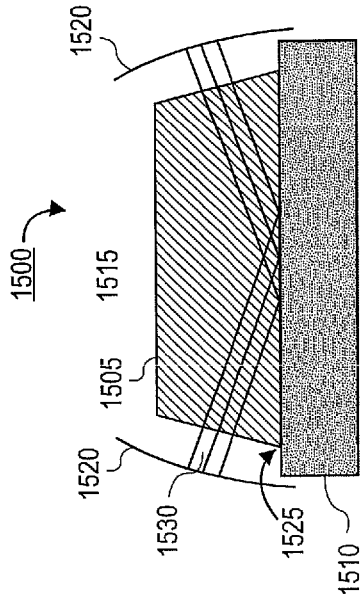
FIGS. 15A-D illustrate various embodiments of resonator cavity excitation devices.
Figure 15D:
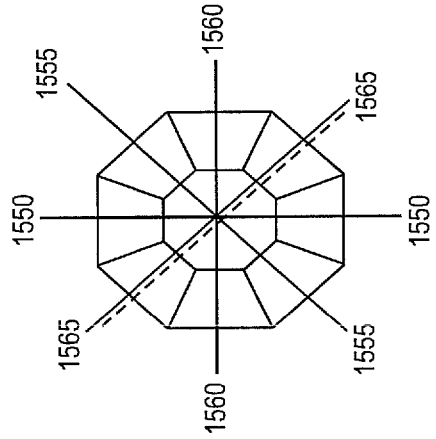
Figure 15A:
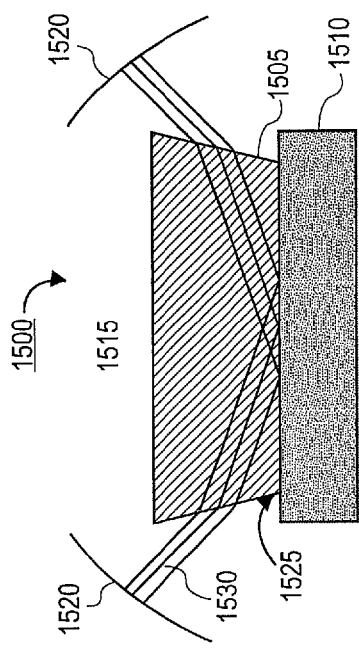
Figure 16A:
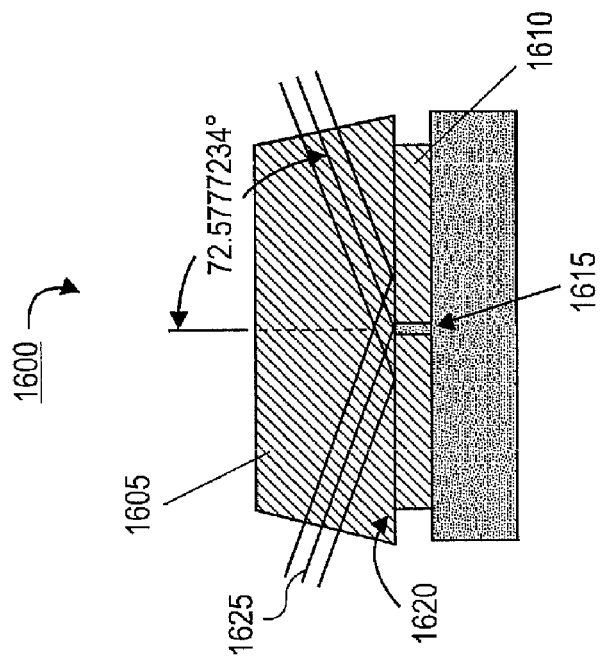
FIGS. 16A-B illustrate angles of light beams in various embodiments of the resonator cavity excitation device.
Figure 16B:
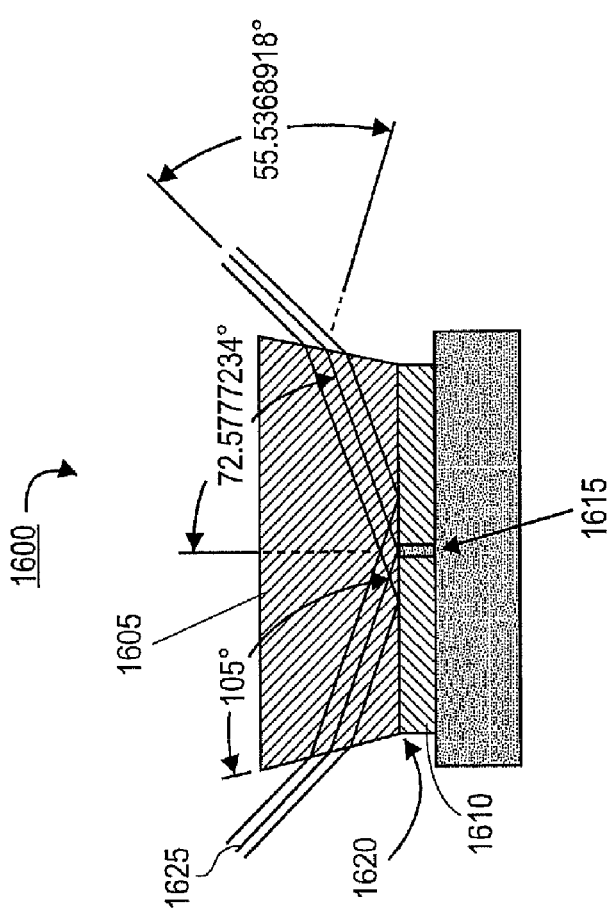

FIG. 15A depicts a resonator cavity where the light beam enters the prism at Brewster's angle, which is depicted in greater detail in FIGS. 16A-B. FIGS. 16A-B illustrates an exemplary resonator cavity excitation device 1600 showing the angles to initiate TIR. As shown in FIG. 16A, the cross-section of excitation device 1600 includes a single hole 1615. The substrate 1605 of the excitation device can be implemented with silica (n=1.457) and the exclusion coating 1610 is implemented with $MgF_2$ (n=1.377). Laser light can be any available color appropriate for the dyes used. For example, 488 nm or 632 nm are commonly available laser colors. Multiple lasers can either be used independently or simultaneously.

Within the substrate 1605, light path 1625 can approach at the critical angle (Brewster's angle) 55.53 degrees to achieve zero-reflection passage from the air to the substrate 1605 The light path 1625 approaches the hole 1615 at the critical angle or greater to induce TIR at the TIR interface 1620. For this embodiment, the critical angle is 71.26 for 633 nm light although the angle of incidence can be larger. The reflected light can exit at the same angle but can deviate depending on the angle of incidence, wavelength of the light, and/or materials.

As depicted in FIG. 16A, the angle of the side wall of the substrate 1605 is 105 degrees from the interface between the substrate 1605 and exclusion coating 1610.

FIG. 16B depicts a resonator cavity excitation device 1600 where the light path 1625 approaches the hole 1615 at the critical angle or greater to induce TIR. For this embodiment, the critical angle is 72.578 degrees from incidence. The reflected light can exit at the same angle but can deviate depending on the angle of incidence, wavelength of the light, and/or materials.

Figure 15C:
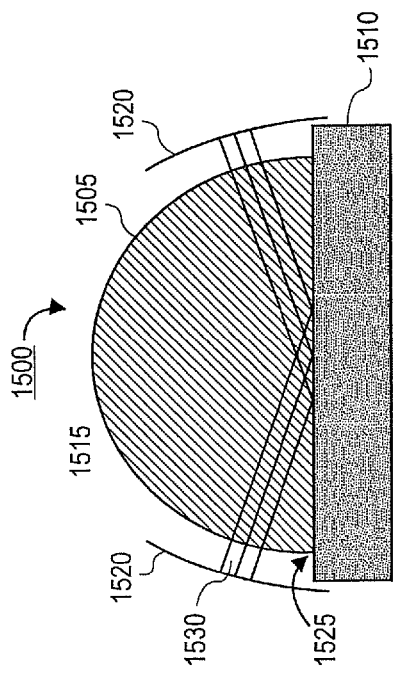

Turning to FIG. 15B, this figure depicts another embodiment of the resonator cavity excitation device where the highly reflective mirrors 1520 of the resonator cavity direct light beam 1525 at normal incidence. Turning to FIG. 15C, this figure depicts yet another embodiment of the resonator cavity excitation device 1500. The substrate 1505 can be configured to be a hemisphere. The highly reflective mirrors 1520 are positioned to let the light beam 1525 enter the substrate 1505 at normal incidence.

Figure 17:
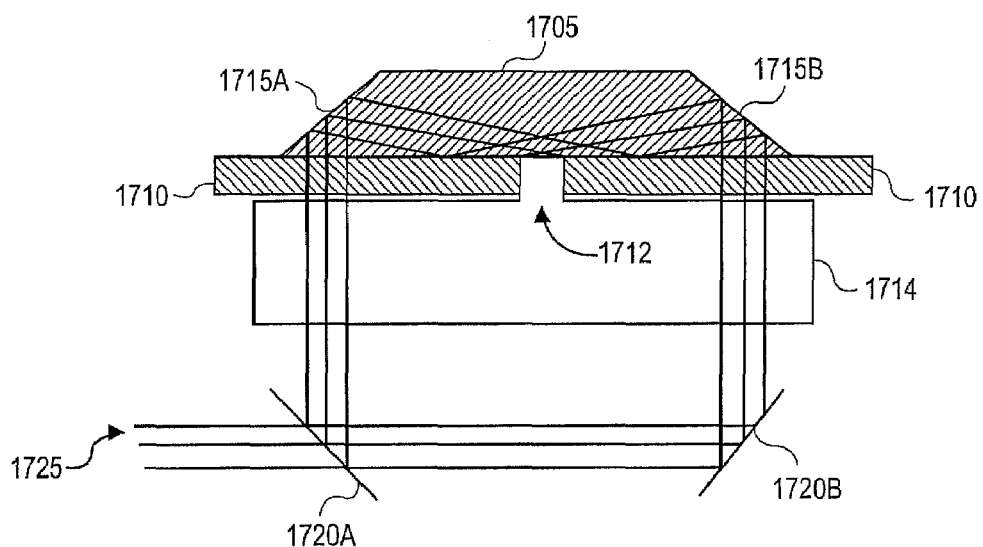
FIG. 17 illustrates a system in accordance with yet another embodiment.

FIG. 15D depicts yet another embodiment of the resonator cavity excitation device 1500. In this embodiment, multiple cavities 1550-1565 can be formed. Each cavity can support a laser at a selected wavelength. Accordingly, for this embodiment, four different wavelengths can be used in detection. It should be readily obvious to one of skilled in the art that any number of cavities can be support without departing with the scope of the invention, FIG. 17 illustrates a system 1700 in accordance with yet another embodiment. As shown in FIG. 17, an excitation device can include substrate 1705 implemented with a silica material and an exclusion coating 1710 implemented with aluminum. A hole 1712 can be formed within the exclusion coating 1710 to interact with a dye solution 1714. The substrate 1705 can be configured to have prism surfaces 1715AB. The system 1700 can also include highly reflective mirrors 1720AB.

During excitation, an input laser can emit coherent light energy 1725 at a selected wavelength through the highly reflective mirror 1720A through an input coupler (not shown). The coherent light energy 1725 from the highly reflective mirror 1720A can be transmitted toward a side of the fixed prism 1715A. The coherent light energy 1725 can also be directed to highly reflective mirror 1720B and reflected toward another side of the prism surface 1715B. The prism surface 1715B can be configured to reflect the light toward the hole 1712.

Figure 18:
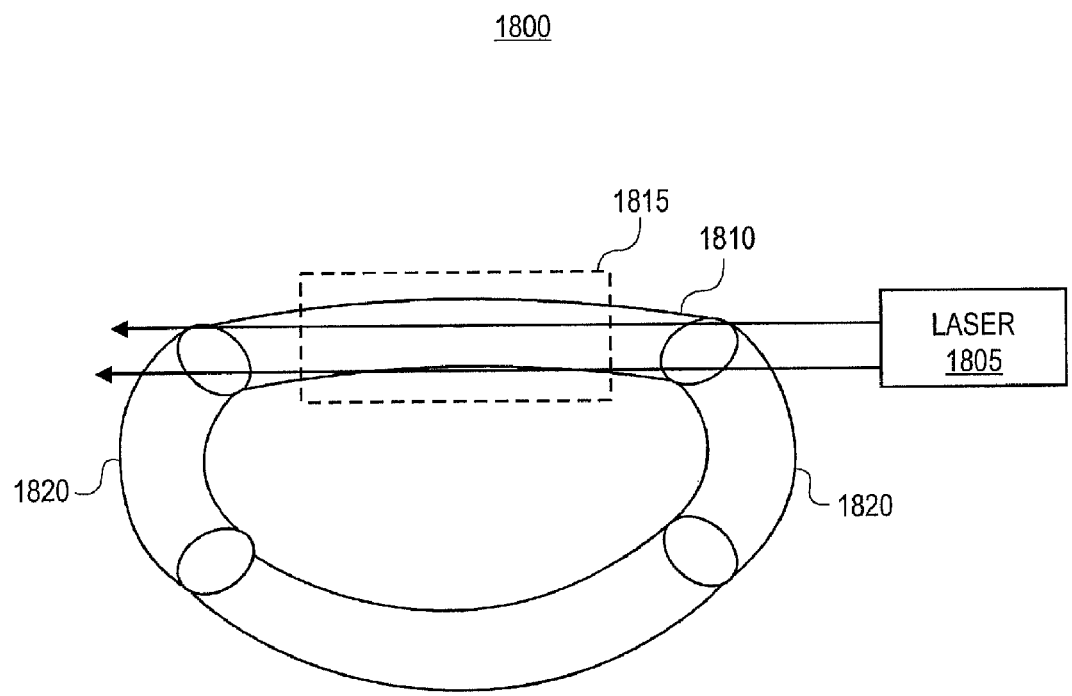
FIG. 18 illustrates a system in accordance with yet another embodiment.

Yet another embodiment uses optical fibers and is depicted in FIG. 18. As shown in FIG. 18, system 1800 includes an excitation device 1805 which launches light down one or more optical fibers 1810. A detection area 1815 may be created over a portion of the fibers 1810. A coating on the fibers can designed to induce evanescent waves of the surface of the fiber. In the detection area 1815, small holes (not shown) may be placed in the coating such that the coating of the fibers 1810 acts as an exclusion coating. The run of optical fiber 1810 can include loops 1820 large enough to preserve TIR.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Those skilled in the art will recognize that these and other variations are possible within the spirit and scope as defined in the following claims and their equivalents.

What is claimed is:

1. A system for analysis of an analyte, the system comprising:
   a substrate;
   an exclusion layer deposited on the substrate, the exclusion layer having a hole reaching a portion of the substrate;
   a fluid sample contacting the substrate through the hole;
   an excitation light source configured to induce an evanescent wave field with a penetration depth that is below a top surface of the exclusion layer, wherein the evanescent wave field energizes a first inorganic absorber bound to the substrate; and
   a detector configured to detect light emissions.

2. The system of claim 1, wherein the inorganic absorber is a quantum dot.

3. The system of claim 1, wherein the inorganic absorber is an upconverting phosphor.

4. The system of claim 1, wherein the evanescent wave is induced by internal reflection.

5. The system of claim 1, wherein the substrate and the fluid sample each have different index of refraction from the other.

6. The system of claim 1, wherein the inorganic absorber creates an energy transfer zone at a first wavelength.

7. The system of claim 6, further comprising:
   an enzyme, wherein a first portion of the enzyme is bound to a fluorescently labeled moiety and a second portion of the enzyme is attached to the first inorganic absorber, wherein the first inorganic absorber transfers excitation energy to the fluorescently labeled moiety at a first wavelength.

8. The system of claim 7, further comprising a second inorganic absorber that is attached to a third portion of the enzyme, wherein the second inorganic absorber is configured to be energized by the evanescent wave field and transfer excitation energy to the fluorescently labeled moiety at a second wavelength.

9. The system of claim 7, wherein the fluorescently labeled moiety includes a fluorescent dye component, a quencher component and a nucleotide component.

10. The system of claim 9, wherein the fluorescent dye component is configured to fluoresce upon cleavage from the quencher component and the nucleotide component.

11. A system for analysis of analyte, the system comprising:
    a transparent substrate coated with a metal layer;
    an exclusion coating deposited on the metal layer;
    a fluorescently labeled molecule configured to diffuse into a hole in the exclusion coating; and
    an excitation light source configured to produce plasmon-coupled emission with a penetration depth that is below a top surface of the exclusion coating.

12. The system of claim 11, wherein the exclusion coating is implemented with an index of refraction material higher than a material of the substrate.

13. The system of claim 11, wherein the plasmon coupled emission form an energy transfer zone in the hole in the exclusion coating.

14. The system of claim 13, wherein a cone of emission light is formed in response the fluorescently labeled molecule entering the energy transfer zone.

15. A luminescence detection system, the system comprising a resonant optical cavity, wherein luminophore emission is elicited by evanescent excitation established within the boundary of the resonant optical cavity.

16. The system of claim 15, wherein the resonant optical cavity further comprises:
    an excitation light source configured to produce light at a selected wavelength;
    a substrate; and
    a plurality of mirrors, wherein one mirror is position to reflect and deflect light from the excitation light source to the substrate which reflects the light to the second mirror, which reflects the light and redirects the light substantially the reverse direction as the incoming light.

17. The system of claim 15, further comprising:
    an excitation light source configured to produce light at a selected wavelength;
    a total internal reflection interface; and
    a plurality of mirrors, wherein the resonant optical cavity is bounded by the plurality of mirrors and the total internal reflection interface.

18. The system of claim 17, wherein the light from the excitation light source enters the resonant optical cavity at the Brewster's angle to induce total internal reflection.

19. The system of claim 17, wherein the light from the excitation light source enters the resonant optical cavity at normal incidence.

20. The system of claim 15, further comprising:
    a plurality of light source, each source configured to produce associated light at a selected wavelength;
    a plurality of total internal reflection interface;
    a plurality of mirrors further comprising of a plurality of subsets of mirrors, each subset of mirrors associated with a light source, wherein a plurality of resonant cavities are formed, each resonant cavity bounded by an associated subset of mirrors and associated total internal reflection interface and supplied with light from an associated light source.

* * * * *